US008741587B2

(12) United States Patent
Roessler et al.

(10) Patent No.: US 8,741,587 B2
(45) Date of Patent: Jun. 3, 2014

(54) ARMET AS A MARKER FOR CANCER

(75) Inventors: Markus Roessler, Germering (DE); Johann Karl, Peissenberg (DE); Julia Riedlinger, Munich (DE); Ingo Lindner, Penzberg (DE); Michael Tacke, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 23 days.

(21) Appl. No.: 13/103,123

(22) Filed: May 9, 2011

(65) Prior Publication Data

US 2011/0212465 A1 Sep. 1, 2011

Related U.S. Application Data

(63) Continuation of application No. PCT/EP2009/009159, filed on Dec. 18, 2009.

(30) Foreign Application Priority Data

Dec. 22, 2008 (EP) ...................................... 08022238

(51) Int. Cl.
*G01N 33/574* (2006.01)
(52) U.S. Cl.
CPC .... *G01N 33/57423* (2013.01); *G01N 33/57484* (2013.01)
USPC ............................ 435/7.23; 435/7.1; 435/6.14
(58) Field of Classification Search
None
See application file for complete search history.

(56) References Cited

U.S. PATENT DOCUMENTS

2004/0005563 A1* 1/2004 Mack et al. ........................ 435/6

FOREIGN PATENT DOCUMENTS

| WO | 2004/057336 A3 | 7/2004 |
| WO | 2004/108964 A1 | 12/2004 |

OTHER PUBLICATIONS

International Search Report issued Mar. 9, 2010 in PCT Application No. PCT/EP2009/009159.
International Preliminary Report on Patentability issued Feb. 11, 2011 in Application No. PCT/EP2009/009159.
Aksoy, Saime et al., "Human Liver Nicotinamide N-Methyltransferase cDNA Cloning, Expression, and Biochemical Characterization," The Journal of Biological Chemistry, May 20, 1994, pp. 14835-14840, vol. 269, No. 20.
Apostolou, Andria et al., "Armet, a UPR-upregulated protein, inhibits cell proliferation and ER stress-induced cell," Experimental Cell Research, 2008, pp. 2454-2467, vol. 314.
Breiman, Leo, "Random Forests," Machine Learning, 2001, pp. 5-32, vol. 45.

Buccheri, Gianfranco and Ferrigno, Domenico, "Identifying Patents at Risk of Early Postoperative Recurrence of Lung Cancer: A New Use of the Old CEA Test," The Annals of Thoracic Surgery, 2003, pp. 973-980, vol. 75.
Drach, Johannes et al., "A cellular proteome map of human multiple myeloma," Database Biosis PREV200800215384, Nov. 2007, 49th Annual Meeting of the American Society of Hematology, Atlanta, GA, 2 pages.
Duffy, M. J., "Clinical Uses of Tumor Markers: A Critical Review," Critical Reviews in Clinical Laboratory Sciences, 2001, pp. 225-262, vol. 38, No. 3.
Friedman, Jerome H., "Regularized Discriminant Analysis," Journal of the American Statistical Association, Mar. 1989, pp. 165-175, vol. 84, No. 405.
Fukasawa, Toshio et al., "Clinical Evaluation of Serum NSE and CEA in Primary Lung Cancer Patients," Japanese Journal of Cancer and Chemotherapy, May 1986, pp. 1862-1867, vol. 13, No. 5.
Kassem, Heba Sh. et al., "A Potential Role of Heat Shock Proteins and Nicotinamide N-Methyl Transferase in Predicting Response to Radiation in Bladder Cancer," International Journal of Cancer, 2002, pp. 454-460, vol. 101.
Merle, P. et al., "Early CYFRA 21-1 variation predicts tumor response to chemotherapy and survival in locally advanced non-small cell lung cancer patients," The International Journal of Biological Markers, 2004, pp. 310-315, vol. 19, No. 4.
Mizobuchi, Naomi et al., "ARMET is a Soluble ER Protein Induced by the Unfolded Protein Response via ERSE-II Element," Cell Structure and Function, 2007, pp. 41-50, vol. 32.
Molina, R. et al., "Tumor Markers (CEA, CA 125, CYFRA 21-1, SCC and NSE) in Patients with Non-Small Cell Lung Cancer as an Aid in Histological Diagnosis and Prognosis Comparison with the Main Clinical and Pathological Prognostic Factors," Tumor Biology, 2003, pp. 209-218, vol. 24.
Okamura, Atsushi et al., "Increased Hepatic Nicotinamide N-Methyltransferase Activity as a Marker of Cancer Cachexia in Mice Bearing Colon 26 Adenocarcinoma," Japanese Journal of Cancer Research, Jun. 1998, pp. 649-656, vol. 89.
Petrova, Penka S. et al., "A New Mesencephalic, Astrocyte-Derived Neurotrophic Factor with Selectivity for Dopaminergic Neurons," Journal of Molecular Neuroscience, 2003, pp. 173-188, vol. 20.
Piepoli, Ada et al., "Lack of association between UGT1A7, UGT1A9, ARP, SPINK1 and CFTR gene polymorphisms and pancreatic cancer in Italian patients," World Journal of Gastroenterology, Oct. 21, 2006, pp. 6343-6348, vol. 12, No. 39.

(Continued)

*Primary Examiner* — Mark Halvorson
(74) *Attorney, Agent, or Firm* — Roche Diagnostics Operations, Inc.

(57) ABSTRACT

Disclosed is a method aiding in the assessment of cancer. More specifically disclosed is the use of the arginine-rich metastasized in early tumors protein (=ARMET) as a universal marker of different cancer types. ARMET aids in the assessment of pulmonary or lung cancer (LC) or of colon cancer, e.g., of non-small cell lung carcinoma (NSCLC) or colorectal cancer (CRC), but also likely of other specific types of cancer. Such specific cancer types are, e.g., breast, ovary, cervix, head and neck, endometrium, melanoma, bladder, kidney, pancreas, prostate, esophagus, stomach or bile duct cancer. Further disclosed is a method for assessing cancer from a liquid sample, derived from an individual by measuring ARMET in the sample. Measurement of ARMET can, e.g., be used in the early detection of cancer or in the surveillance of patients who undergo surgery.

9 Claims, 12 Drawing Sheets

(56) References Cited

OTHER PUBLICATIONS

Ruczinski, Ingo et al., "Logic Regression," Journal of Computational and Graphical Statistics, 2003, pp. 475-511, vol. 12, No. 3.

Schneider, Joachim et al., "Fuzzy logic-based tumor-marker profiles improved sensitivity in the diagnosis of lung cancer," International Journal of Clinical Oncology, 2002, pp. 145-151, vol. 7.

Shridhar, Ravi et al., "Mutations in the Arginine-rich Protein Gene, in Lung, Breast, and Prostate Cancers, and in Squamous Cell Carcinoma of the Head and Neck," Cancer Research, Dec. 15, 1996, pp. 5576-5578, vol. 56.

Shridhar, Viji et al., "A gene from human chromosomal band 3p21.1 encodes a highly conserved arginine-rich protein and is mutated in renal cell carcinomas," Oncogene, 1996, pp. 1931-1939, vol. 12.

Shridhar, Viji et al., "Mutations in the arginine-rich protein gene (ARP) in pancreatic cancer," Oncogene, 1997, pp. 2213-2216, vol. 14.

Tanaka, Hisashiu et al., "Polymorphic variation of the ARP gene on 3p21 in Japanese esophageal cancer patients," Oncology Reports, 2000, pp. 591-593, vol. 7.

Wagner, Henry Jr., "Postoperative Adjuvant Therapy for Patients With Resected Non-Small Cell Lung Cancer: Still Controversial After all These Years," Chest, 2000, pp. 110S-118S, vol. 117.

Zweig, Mark H. and Campbell, Gregory, "Receiver-Operating Characteristic (ROC) Plots: A Fundamental Evaluation Tool in Clinical Medicine," Clinical Chemistry, 1993, pp. 561-577, vol. 39, No. 4.

\* cited by examiner

Fig. 6

```
  1  MWATQGLAVA LALSVLPGSR ALRPGDCEVC ISYLGRFYQD LKDRDVTFSP
 51  ATIENELIKF CREARGKENR LCYYIGATDD AATKIINEVS KPLAHHIPVE
101  KICEKLKKKD SQICELKYDK QIDLSTVDLK KLRVKELKKI LDDWGETCKG
151  CAEKSDYIRK INELMPKYAP KAASARTDL
```

ARMET AS A MARKER FOR CANCER

RELATED APPLICATIONS

This application is a continuation of PCT/EP2009/009159 filed Dec. 18, 2009 and claims priority to EP 08022238.3 filed Dec. 22, 2008.

SEQUENCE LISTING

The instant application contains a Sequence Listing which has been submitted in ASCII format via EFS-Web and is hereby incorporated by reference in its entirety. Said ASCII copy, created on May 5, 2011, is named 25734US.txt, and is 2,806 bytes in size.

FIELD OF THE INVENTION

The present invention relates to a method aiding in the assessment of cancer. It discloses the use of the arginine-rich mutated in early stage tumors protein (=ARMET) as a universal marker of different cancer types. ARMET aids in the assessment of pulmonary or lung cancer (LC) or of colon cancer, e.g., of non-small cell lung carcinoma (NSCLC) or colorectal cancer (CRC), but also likely of other specific types of cancer. Such specific cancer types are, e.g., breast, ovary, cervix, head and neck, endometrium, melanoma, bladder, kidney, pancreas, prostate, esophagus, stomach or bile duct cancer. Furthermore, it especially relates to a method for assessing cancer from a liquid sample, derived from an individual by measuring ARMET in said sample. Measurement of ARMET can, e.g., be used in the early detection of cancer or in the surveillance of patients who undergo surgery.

BACKGROUND OF THE INVENTION

Cancer remains a major public health challenge despite progress in detection and therapy. Cancer cells are characterized by the production of cancer-associated marker proteins. Cancer-associated proteins are found both in the tissues and in the bodily fluids of an individual who carries cancer cells. Their levels usually are low at the early stages of the carcinogenic progress and increase during the disease's progression and only in rare cases proteins are observed showing a decreased level in the course of disease progression. The sensitive detection of these proteins is an advantageous and promising approach for the diagnosis of cancer, in particular in an early stage diagnosis of cancer. The most prevalent cancer types are breast cancer (BC), lung cancer (LC) and colorectal cancer (CRC).

The most important therapeutic approaches for solid tumors are:
a) surgical resection of the tumor,
b) chemotherapy,
c) radiation therapy,
d) treatment with biologicals, like anti-tumor antibodies or anti-angiogenic antibodies and
e) a combination of the above methods.

Surgical resection of the tumors is widely accepted as a first line treatment for early stage solid tumors. Most cancers, however, are detected only when they become symptomatic, i.e. when patients already are in a rather late stage of disease progression.

The staging of cancer is the classification of the disease in terms of extent, progression, and severity. It groups cancer patients so that generalizations can be made about prognosis and the choice of therapy.

The different stages of CRC used to be classified according to Dukes' stages A to D. Today, the TNM system is the most widely used classification of the anatomical extent of cancer. It represents an internationally accepted, uniform staging system. There are three basic variables: T (the extent of the primary tumor), N (the status of regional lymph nodes) and M (the presence or absence of distant metastases). The TNM criteria are published by the UICC (International Union Against Cancer), Sobin, L. H., Wittekind, Ch. (eds.), TNM Classification of Malignant Tumours, sixth edition (2002)). Once the TNM status is determined the patients are grouped into disease stages that are denoted by Roman numerals ranging form I to IV with IV being the most advanced disease stage. TNM staging and UICC disease stages correspond to each other as shown in the following table taken from Sobin and Wittekind (eds.), supra.

| Interrelation of TNM staging and UICC disease stages | | | |
|---|---|---|---|
| UICC disease stage | T staging | N staging | M staging |
| Stage 0 | Tis | N0 | M0 |
| Stage I | T1, T2 | N0 | M0 |
| Stage IIA | T3 | N0 | M0 |
| Stage IIB | T4 | N0 | M0 |
| Stage IIIA | T1, T2 | N1 | M0 |
| Stage IIIB | T3, T4 | N1 | M0 |
| Stage IIIC | Any T | N2 | M0 |
| Stage IV | Any T | Any N | M1 |

What is especially important is that early diagnosis cancer, e.g., of CRC translates to a much better prognosis. In CRC malignant tumors of the colorectum arise from benign tumors, i.e. from adenoma. Therefore, best prognosis have those patients diagnosed at the adenoma stage. Patients diagnosed as early as in stage Tis, N0, M0 or T1-3; N0; M0, if treated properly have a more than 90% chance of survival 5 years after diagnosis as compared to a 5-years survival rate of only 10% for patients diagnosed when distant metastases are already present.

Current detection methods including imaging methods, such as X-ray or nuclear resonance imaging in theory might at least partially be appropriate for use as a general screening tool. However, they are very costly and not affordable to health care systems for a general and broad use in mass screenings of large numbers of subjects, particularly for subjects without any tumor symptoms.

Thus, it is an object of the present invention to provide a simple and cost-efficient procedure of tumor assessments, e.g., to identify individuals suspect of having cancer. For this purpose, a general tumor marker which is detectable in body fluids, e.g., blood or serum or plasma or a panel of such markers, would be desirable.

A number of serum tumor markers are already in clinical use. For example the soluble 30 kDa fragment of cytoceratin 19 (CYFRA 21-1), carcinoembryogenic antigen (CEA), neuron-specific enolase (NSE), and squamous cell carcinoma antigen (SCC) are the most prominent LC markers. However, none of them meets the criteria for sensitivity and specificity required for a screening tool (Thomas, L., Labor and Diagnose, T H Books Verlagsgesellschaft, Frankfurt/Main, Germany (2000)).

In order to be of clinical utility, a new diagnostic marker as a single marker should be comparable to other markers known in the art, or better. Or, a new marker should lead to a progress in diagnostic sensitivity and/or specificity either if used alone or in combination with one or more other markers, respectively. The diagnostic sensitivity and/or specificity of a test is best assessed by its receiver-operating characteristics, which will be described in detail below.

Whole blood, serum or plasma are the most widely used sources of sample in clinical routine. The identification of an early tumor marker that would aid in the reliable cancer detection or provide early prognostic information could lead to a method that would greatly aid in the diagnosis and in the management of this disease. Therefore, an urgent clinical need exists to improve the in vitro assessment of cancer and in particular of LC. It is especially important to improve the early diagnosis of cancer, e.g., LC, since for patients diagnosed early on chances of survival are much higher as compared to those diagnosed at a progressed stage of disease.

The clinical utility of biochemical markers in lung cancer has recently been reviewed (Duffy, M. J., Crit. Rev. Clin. Lab. Sci. 38 (2001) 225-262).

CYFRA 21-1 is currently regarded to be the best of the presently known tumor markers for lung cancer. Even though not organ-specific it is predominantly found in lung tissue. Sensitivity of CYFRA 21-1 for lung cancer is described to be between 46-61% at a specificity of 95% towards other benign lung diseases. Increased serum levels of CYFRA 21-1 are also associated with pronounced benign liver diseases, renal insufficiency and invasive bladder cancer. CYFRA 21-1 testing is recommended for postoperative therapy surveillance.

CEA belongs to the group of carcinofetal antigens, usually produced during embryogenesis. CEA is not organ-specific and predominantly used for monitoring of colorectal cancer. Besides malignancies, also several benign diseases such as cirrhosis, bronchitis, pancreatitis and autoimmune diseases are associated with increased CEA serum levels. At 95% specificity towards benign lung diseases its sensitivity for lung cancer is reported to be 29-44%. The primary use of CEA is in monitoring colon cancer, especially when the disease has metastasized. However, a variety of cancers can produce elevated levels of CEA, including breast cancer. A preferred use of CEA is therapy surveillance of lung cancer.

NSE is a tumor marker for SCLC. Generally, increased NSE serum levels are found in association with neuroectodermal and neuroendocrine tumors. Increased serum levels are also found in patients with benign lung diseases and cerebral diseases, such as meningitis or other inflammatory diseases of the brain, and traumatic injuries to the head. While sensitivity for SCLC at 95% specificity is reported to be 60-87%, performance of NSE testing for NSCLC is poor (7-25%). NSE is recommended for therapy surveillance of SCLC.

CA 19-9 (carbohydrate antigen 19-9), a sialylated Lewis (a) antigen on a glycolipid is a tumor marker for gastrointestinal cancers. It occurs in fetal gastric, intestinal and pancreatic epithelia. Low concentrations can also be found in adult tissue in the liver, lungs, and pancreas. There is no correlation between tumor mass and the CA 19-9 assay values Therefore the determination of CA 19-9 cannot be used for the early detection of pancreatic carcinoma. As the mucin is excreted exclusively via the liver, even slight cholestasis can lead to clearly elevated CA 19-9 serum levels in some cases. The marker is mainly used as an aid in the monitoring of disease status in those patients having confirmed pancreatic cancer (sensitivity 70-87%). 3-7% of the population have the Lewis a-negative/b-negative blood group configuration and are unable to express the mucin with the reactive determinant CA 19-9. This must be taken into account when interpreting the findings.

CA 125 is found in a high percentage of non-mucinous ovarian tumors of epithelial origin and can be detected in serum. Ovarian carcinoma accounts for about 20% of gynecological tumors. Although the highest CA 125 values occur in patients suffering from ovarian carcinoma, clearly elevated values are also observed in malignancies of the endometrium, breast, gastrointestinal tract, and various other malignancies. Increased values are sometimes found in various benign gynecological diseases such as ovarian cysts, ovarian metaplasia, endometriosis, uterus myomatosus or cervicitis. Slight elevations of this marker may also occur in early pregnancy and in various benign diseases (e.g., acute and chronic pancreatitis, benign gastrointestinal diseases, renal insufficiency, autoimmune diseases and others). Markedly elevated levels have been found in benign liver diseases such as cirrhosis and hepatitis. Extreme elevations can occur in any kind of ascites due to malignant and benign diseases. Although CA 125 is a relatively unspecific marker, it is today the most important tumor marker for monitoring the therapy and progress of patients with serous ovarian carcinoma. A sensitivity of 69-79% is reported for 82-93% specificity.

PSA ("prostate specific antigen") is commonly tested tumor marker used in blood testing. PSA appears to have a high tissue specificity; the glycoprotein is found in normal prostatic epithelium and secretions but not in other tissues. PSA is highly sensitive for the presence of prostatic cancer. The elevation correlated with stage and tumor volume. It is predictive of recurrence and response to treatment. Finally, the antigen has prognostic value in patients with very high values prior to surgery are likely to relapse.

NNMT (nicotinamide N-methyltransferase; Swiss-PROT: P40261) has an apparent molecular weight of 29.6 kDa and an isoelectric point of 5.56. NNMT catalyzes the N-methylation of nicotinamide and other pyridines. This activity is important for biotransformation of many drugs and xenobiotic compounds. The protein has been reported to be predominantly expressed in liver and is located in the cytoplasm. NNMT has been cloned from cDNA from human liver and contained a 792-nucleotide open reading frame that encoded a 264-amino acid protein with a calculated molecular mass of 29.6 kDa (Aksoy, S., et al., J. Biol. Chem. 269 (1994) 14835-14840). Little is known in the literature about a potential role of the enzyme in human cancer. In one paper, increased hepatic NNMT enzymatic activity was reported as a marker for cancer cachexia in mice (Okamura, A., et al., Jpn. J. Cancer Res. 89 (1998) 649-656). In a recent report, down-regulation of the NNMT gene in response to radiation in radiation sensitive cell lines was demonstrated (Kassem, H., et al., Int. J. Cancer 101 (2002) 454-460). It has recently been found (WO 2004/057336) that NNMT will be of interest in the assessment of CRC.

ProGRP is a tumor marker, useful in the detection and monitoring of SCLC. Increased serum levels are also found in patients with nonmalignant lung/pleural diseases, such as idiopathic pulmonary fibrosis or sarcoidosis. While sensitivity for proGRP in the field of SCLC (at 95% specificity) is reported to be 47-86%, the performance of proGRP testing in the field of NSCLC is poor because the sensitivity is reported as being below 10%).

SCC (squamous cell carcinoma antigen) was originally identified in squamous cell CA of the cervix. The sensitivity of SCC for LC in general is low (18-27%). Therefore, SCC testing is regarded to be not suitable for screening. However, due to a higher sensitivity for squamous cell CA, a preferred use for SCC is therapy surveillance, even though CYFRA 21-1 generally performs better.

With respect to marker profiles and aiming at improved diagnosis of lung cancer, a method was published (Schneider, J. et al., Int. J. Clin. Oncol. 7 (2002) 145-151) using fuzzy logic based classification algorithms to combine serum levels of CYFRA 21-1, NSE and C-reactive protein (CRP) which is a general inflammation marker. The authors report a sensitivity of 92% at a specificity of 95%. However in this study, for example the sensitivity of CYFRA 21-1 as a single tumor marker is reported to be at 72% at a specificity of 95%, which is significantly higher than in many other reported studies. Duffy, M. J., in Crit. Rev. Clin. Lab. Sci. 38 (2001) 225-262, report a sensitivity of between 46% and 61%. This unusual high performance achieved by Schneider et al., raises some doubts and might be due to several facts. Firstly, the collective of control patients seems to be younger than the patients collective, i.e. the groups are not well age-matched, and the patient collective comprises many late stages. Secondly and even more critical, the performance of the algorithm is checked on the samples of the training set which were used for the determination of the fuzzy logic qualifiers. Hence, these qualifiers are strictly speaking "tailor-made" for this set and not applied to an independent validation set. Under normal circumstances, is has to be expected that the same algorithm applied to a larger, independent, and well balanced validation set will lead to a significantly reduced overall performance.

It was the task of the present invention to investigate whether a biochemical marker can be identified which may be used in assessing cancer disease. In particular, the inventors of the present invention investigated whether a biochemical marker could be identified for the assessment of different cancer types, such as lung, colon, breast, ovary, cervix, head and neck, endometrium, melanoma, bladder, kidney, pancreatic, prostate, esophagus, stomach and/or bile duct cancer in tissue samples or body fluids.

Surprisingly, it has been found that use of the ARMET protein as biomarker can at least partially overcome some of the problems of the markers presently known in the state of the art.

SUMMARY OF THE INVENTION

The present invention relates to a method for assessing cancer in vitro comprising measuring in a sample the concentration of an ARMET protein and/or fragments thereof and using the measurement results, particularly the concentration determined in the assessment of cancer.

Surprisingly, it was found that a increased concentration of an ARMET protein and/or fragments thereof in the test sample is associated with the occurrence of cancer. It could be shown that ARMET is a marker which is not specific for a single type of cancer, but a marker for different types of cancer, i.e. a general tumor marker. Since ARMET appears to be rather specific for tumorigenic processes, the novel tumor marker ARMET has great potential to be of clinical utility with various classes of tumor types.

The method of the present invention is suitable for the assessment of many different types of cancer. Increased concentrations of ARMET protein and/or fragments thereof in a sample as compared to normal controls have been found for example in specific cancer types like lung, colon, breast, ovary, cervix, head and neck, endometrium, melanoma, bladder, kidney, pancreatic, prostate, esophagus, stomach and/or bile duct cancer, respectively.

According to a preferred embodiment of the invention, the concentration of ARMET protein and/or fragments thereof is measured in a sample in order to assess specific cancer types, such as lung, colon, breast, ovary, cervix, head and neck, endometrium, melanoma, bladder, kidney, pancreatic, prostate, esophagus, stomach or bile duct cancer in vitro.

According to another preferred embodiment of the invention, the concentration of ARMET protein and/or fragments thereof is measured in a sample in order to assess cancer, such as lung, colon, breast, ovary, cervix, head and neck, endometrium, melanoma, bladder, kidney, pancreatic or prostate cancer in vitro.

According to another preferred embodiment of the invention, the concentration of ARMET protein and/or fragments thereof is measured in a sample in order to assess cancer, such as lung, colon, breast, ovary, cervix, head and neck, endometrium or melanoma cancer in vitro.

According to another preferred embodiment of the invention, the concentration of ARMET protein and/or fragments thereof is measured in a sample in order to assess cancer, such as lung, colon, breast, cervix, endometrium or ovary cancer in vitro.

According to another preferred embodiment of the invention, the concentration of ARMET protein and/or fragments thereof is measured in a sample in order to assess cancer, such as lung, colon, breast or ovary cancer in vitro.

According to another preferred embodiment of the invention, the concentration of ARMET protein and/or fragments thereof is measured in a sample in order to assess cancer, such as lung cancer (LC) or colorectal cancer (CRC) in vitro.

According to another preferred embodiment of the invention, the concentration of ARMET protein and/or fragments thereof is measured in a sample in order to assess cancer, such as lung cancer (LC) in vitro.

According to another preferred embodiment of the invention, the concentration of ARMET protein and/or fragments thereof is measured in a sample in order to assess cancer, such as colorectal cancer (CRC) in vitro.

One embodiment of the present invention refers to the mass screening of a population to distinguish between individuals which are probably free from cancer and individuals which might be classified as "suspect" cases. The latter group of individuals could then be subjected to further diagnostic procedures, e.g., by imaging methods or other suitable means.

A further embodiment of the present invention refers to an improvement of tumor marker panels which are suitable for the diagnosis of cancer in general or tumor marker panels which are suitable for the diagnosis of a specific tumor type, e.g., lung cancer.

The present invention is also directed to a method for assessing cancer in vitro by biochemical markers, comprising measuring in a sample the concentration of ARMET protein and/or fragments thereof and of one or more other markers specific for cancer, and using the measurement results, particularly the concentrations, determined in the assessment of cancer. Preferred markers for use in combination with ARMET are, on the one hand, markers which are general tumor markers (i.e. markers which are not specific for a single tumor type) or, on the other hand, specific tumor markers (markers which are specific for a single tumor type). Preferred markers, e.g., for the assessment of cancer, such as lung cancer or colon cancer, are Cyfra 21-1, CEA, NSE, CA 19-9, CA 125, PSA, proGRP, SCC and NNMT. These markers may be used individually each or in any combination together with ARMET.

If, according to this method of the invention, cancer is assessed, the one or more other marker of the respective cancer is preferably selected from the group consisting of Cyfra 21-1, CEA, NSE, CA 19-9, CA 125, PSA, proGRP, SCC and NNMT.

Hence, the present invention, in a preferred embodiment, also relates to the use of a marker panel comprising at least the marker ARMET and at least one other tumor marker, e.g., of Cyfra 21-1, CEA, NSE, CA 19-9, CA 125, PSA, proGRP, SCC and NNMT, in the assessment of cancer, e.g., lung and/or colon cancer.

Preferably, the present invention is directed to a method for assessing cancer, such as lung cancer or colon cancer in vitro by biochemical markers, comprising measuring in a sample the concentration of ARMET and/or fragments thereof and of one or more other cancer markers, e.g., one or more other markers of lung or colon cancer and using the measurement results, particularly concentrations determined in the assessment of cancer. It is preferred that the one or more other marker is selected from the group consisting of Cyfra 21-1, CEA, NSE, CA 19-9, CA 125, PSA, proGRP, SCC and NNMT.

The present invention, in a preferred embodiment, also relates to the use of a marker panel comprising at least ARMET and CYFRA 21-1 in the assessment of cancer, particularly LC or colon cancer, and more particularly NSCLC or colorectal cancer.

The present invention also relates to the use of a marker panel comprising at least ARMET and CEA in the assessment of cancer, particularly LC or colon cancer, and more particularly NSCLC or colorectal cancer.

The present invention also relates to the use of a marker panel comprising at least ARMET and NSE in the assessment of cancer, particularly LC or colon cancer, and more particularly NSCLC or colorectal cancer.

The present invention also relates to the use of a marker panel comprising at least ARMET and CA 19-9 in the assessment of cancer, particularly LC or colon cancer, and more particularly NSCLC or colorectal cancer.

The present invention also relates to the use of a marker panel comprising at least ARMET and CA 125 in the assessment of cancer, particularly LC or colon cancer, and more particularly NSCLC or colorectal cancer.

The present invention also relates to the use of a marker panel comprising at least ARMET and PSA in the assessment of cancer, particularly LC or colon cancer, and more particularly NSCLC or colorectal cancer.

The present invention also relates to the use of a marker panel comprising at least ARMET and proGRP in the assessment of cancer, particularly LC or colon cancer, and more particularly NSCLC or colorectal cancer.

The present invention also relates to the use of a marker panel comprising at least ARMET and SCC in the assessment of cancer, particularly LC or colon cancer, and more particularly NSCLC or colorectal cancer.

The present invention also relates to the use of a marker panel comprising at least ARMET and NNMT in the assessment of cancer, particularly LC or colon cancer, and more particularly NSCLC or colorectal cancer. The present invention also relates to the use of an ARMET protein and/or fragments thereof in the assessment of cancer, wherein a increased concentration of ARMET and/or fragments thereof is indicative for cancer.

The present invention also relates to the use of ARMET in the assessment of several specific types of cancer, particularly lung, colon, breast, ovary, cervix, head and neck, endometrium, melanoma, bladder, kidney, pancreatic, prostate, esophagus, stomach and/or bile duct cancer.

The present invention also relates to the use of an antibody directed against an ARMET protein and/or fragments thereof in the assessment of cancer, wherein a increased concentration of ARMET and/or fragments thereof is indicative for cancer.

The present invention also provides a kit for performing the method according to the present invention comprising at least the reagents required to specifically measure an ARMET protein and/or fragments thereof and one or more other marker of cancer.

The present invention also provides a kit for performing the method according to the present invention comprising at least the reagents required to specifically measure ARMET protein and/or fragments thereof and optionally one or more markers of cancer, e.g., markers of lung, colon, breast, ovary, cervix, head and neck, endometrium, melanoma, bladder, kidney, pancreatic, prostate, esophagus, stomach and/or bile duct cancer, as described above, wherein the other markers may be each used individually or in any combination thereof.

The present invention also provides a kit for performing the method according to the present invention comprising at least the reagents required to specifically measure ARMET and CYFRA 21-1, respectively, and optionally auxiliary reagents for performing the measurement.

The present invention also provides a kit for performing the method according to the present invention comprising at least the reagents required to specifically measure ARMET and CEA, respectively, and optionally auxiliary reagents for performing the measurement.

The present invention also provides a kit for performing the method according to the present invention comprising at least the reagents required to specifically measure ARMET and NSE, respectively, and optionally auxiliary reagents for performing the measurement.

The present invention also provides a kit for performing the method according to the present invention comprising at least the reagents required to specifically measure ARMET and CA 19-9, respectively, and optionally auxiliary reagents for performing the measurement.

The present invention also provides a kit for performing the method according to the present invention comprising at least the reagents required to specifically measure ARMET and CA 125, respectively, and optionally auxiliary reagents for performing the measurement.

The present invention also provides a kit for performing the method according to the present invention comprising at least the reagents required to specifically measure ARMET and PSA, respectively, and optionally auxiliary reagents for performing the measurement.

The present invention also provides a kit for performing the method according to the present invention comprising at least the reagents required to specifically measure ARMET and proGRP, respectively, and optionally auxiliary reagents for performing the measurement.

The present invention also provides a kit for performing the method according to the present invention comprising at least the reagents required to specifically measure ARMET and SCC, respectively, and optionally auxiliary reagents for performing the measurement.

The present invention also provides a kit for performing the method according to the present invention comprising at least the reagents required to specifically measure ARMET and NNMT, respectively, and optionally auxiliary reagents for performing the measurement.

In a preferred embodiment the present invention relates to a method for assessing cancer in vitro comprising measuring in a sample the concentration of a) an ARMET protein and/or fragments thereof, b) optionally one or more other marker of cancer, and (c) using the measurement results of step (a) and optionally of step (b) in the assessment of cancer, wherein an increased concentration of ARMET protein and/or fragments thereof is indicative for cancer.

B=panel B, tumor sample;

A=panel A, control sample.

Figure 2:
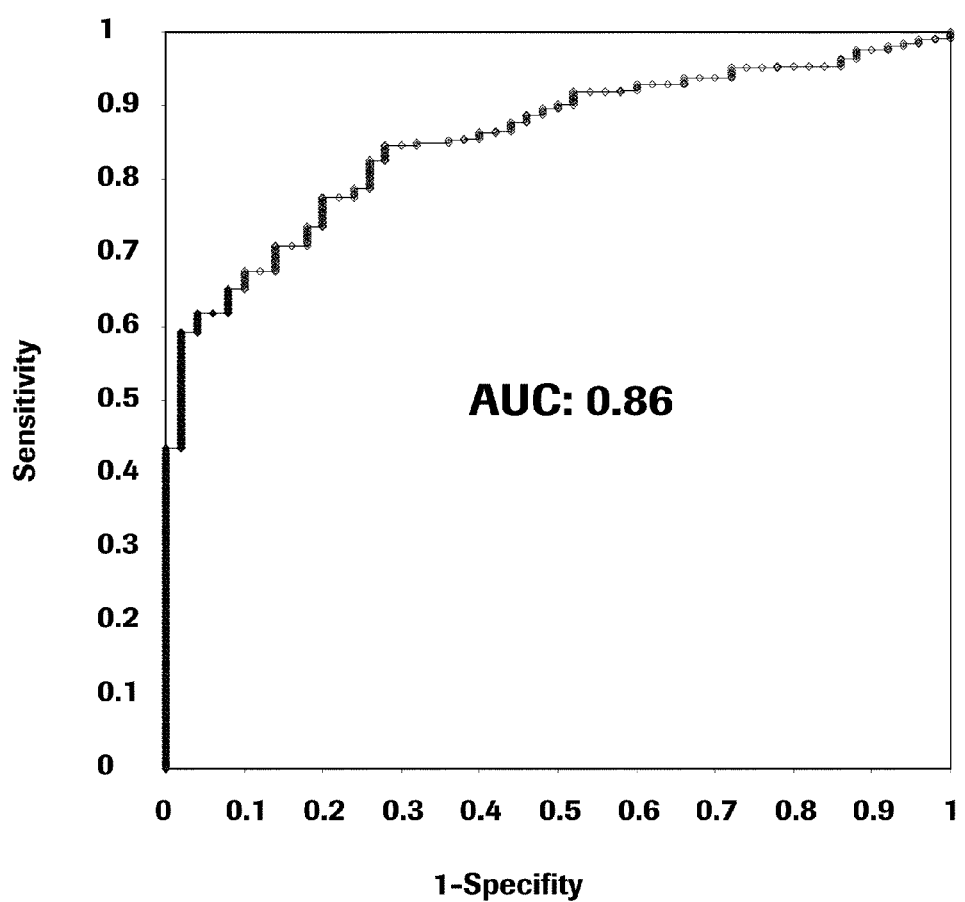

FIG. 2 shows the plot of the receiver operator characteristics (ROC-plot) of ARMET in LC samples with an AUC of 0.86 for the assessment of 366 samples obtained from patients with LC as compared to 50 control samples obtained from obviously healthy individuals.

Figure 3:
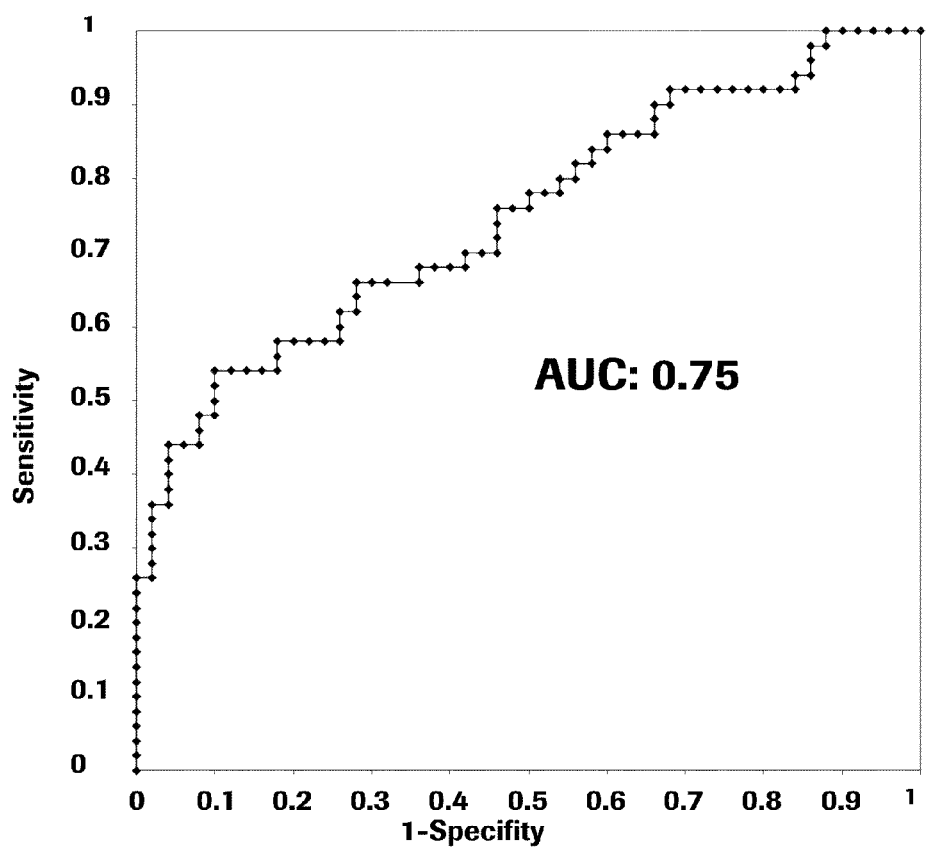

FIG. 3 shows the plot of the receiver operator characteristics (ROC-plot) of ARMET in CRC samples with an AUC of 0.75 for the assessment of 50 samples obtained from patients with CRC as compared to 50 control samples obtained from obviously healthy individuals.

Figure 4:
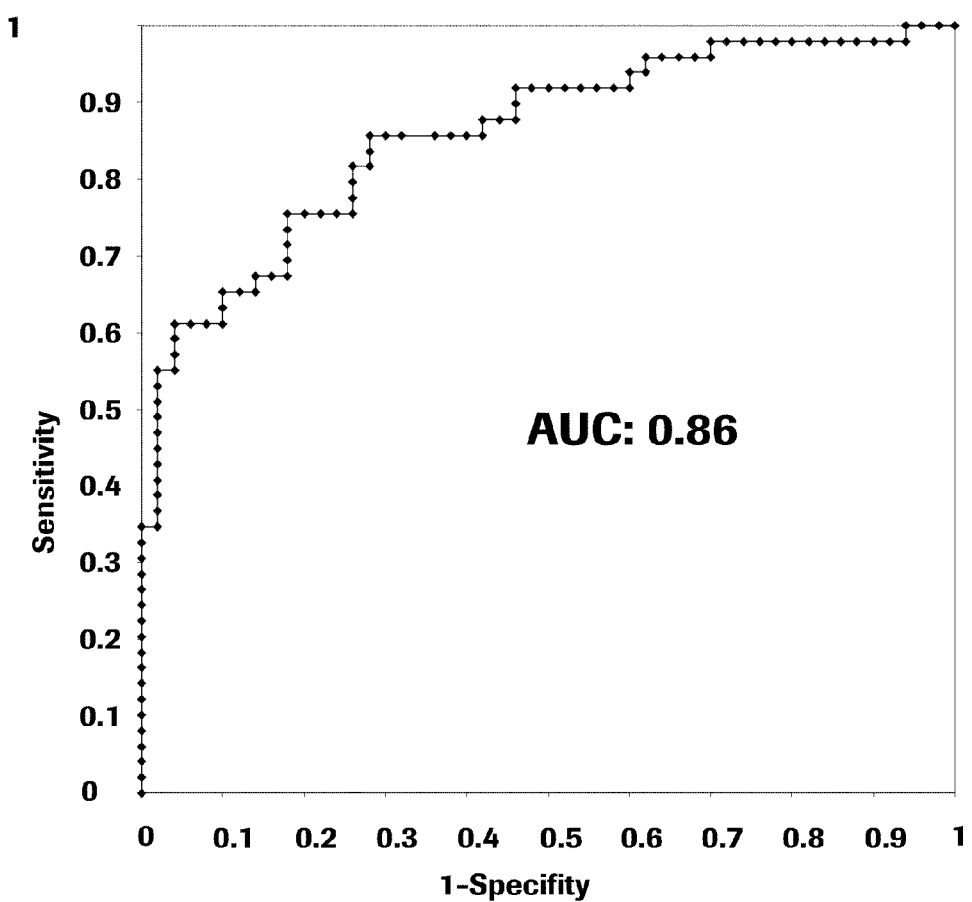

FIG. 4 shows the plot of the receiver operator characteristics (ROC-plot) of ARMET in BC samples with an AUC of 0.86 for the assessment of 49 samples obtained from patients with breast cancer as compared to 50 control samples obtained from obviously healthy individuals.

Figure 5:
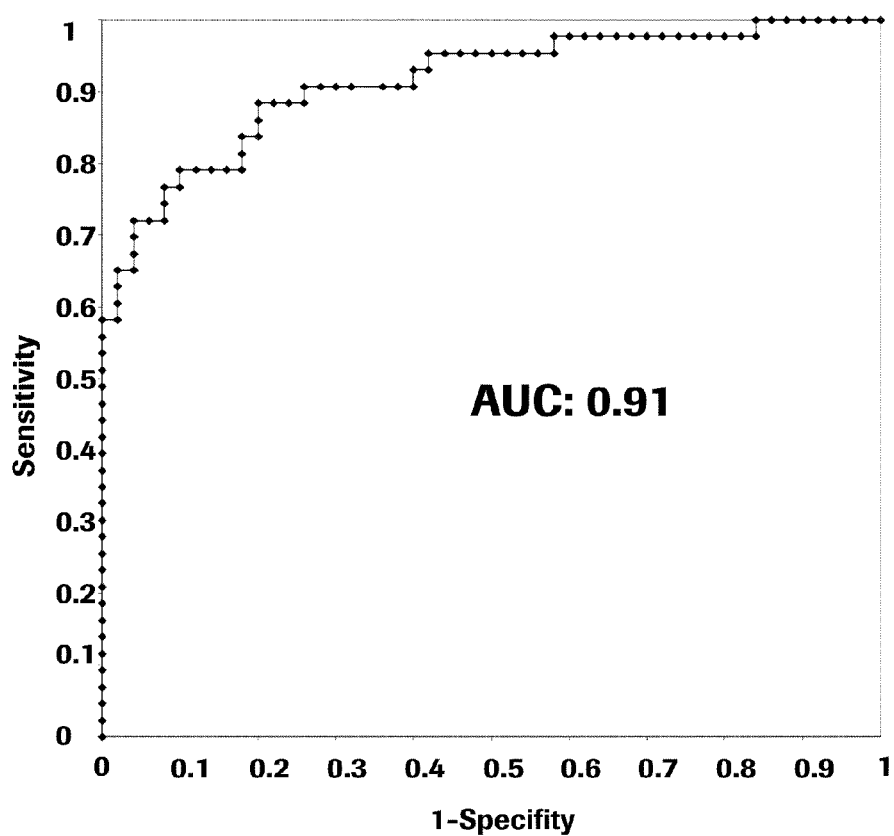

FIG. 5 shows the plot of the receiver operator characteristics (ROC-plot) of ARMET in OC samples with an AUC of 0.91 for the assessment of 43 samples obtained from patients with ovarian cancer as compared to 50 control samples obtained from obviously healthy individuals.

FIG. 6 shows the amino acid sequence of human ARMET protein (SEQ ID NO:1).

Figure 7:
Figure 7A:
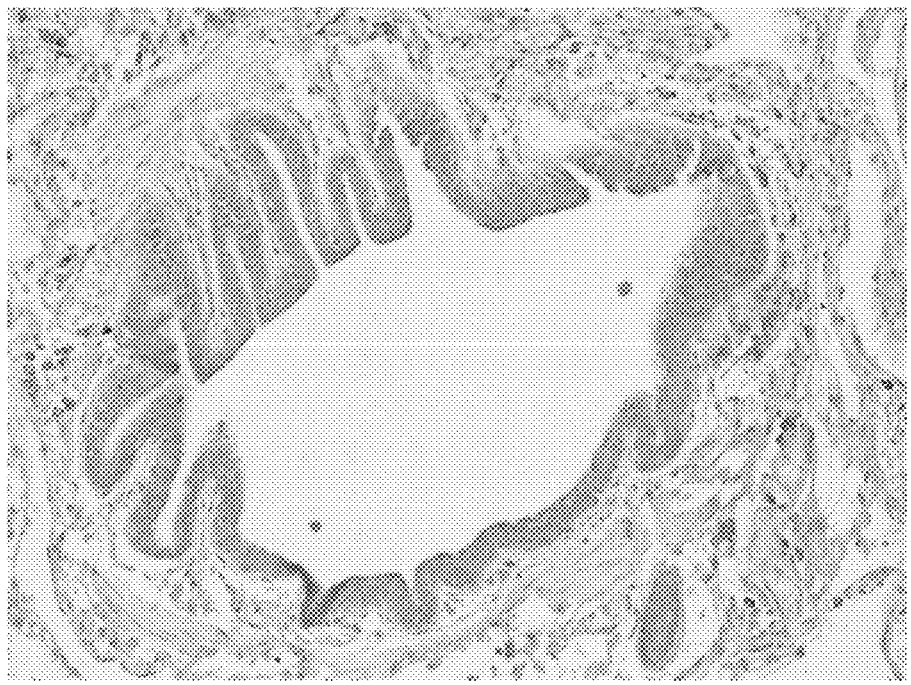
Figure 8:
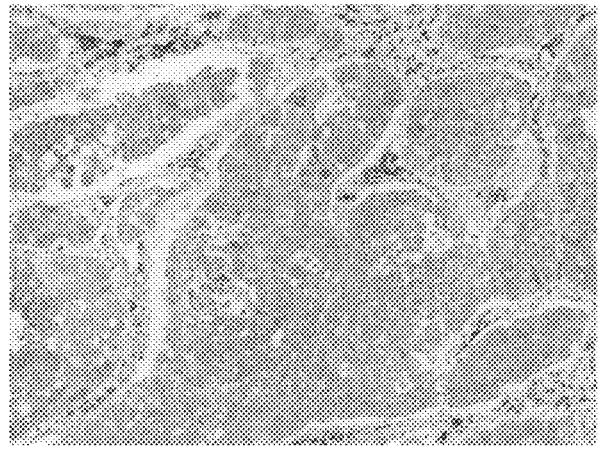
Figure 8A:
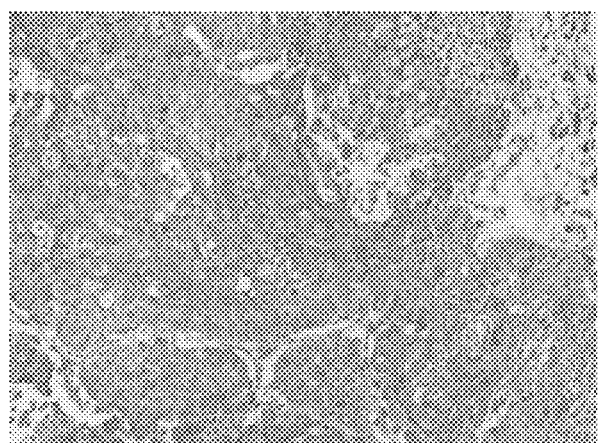
Figure 8B:
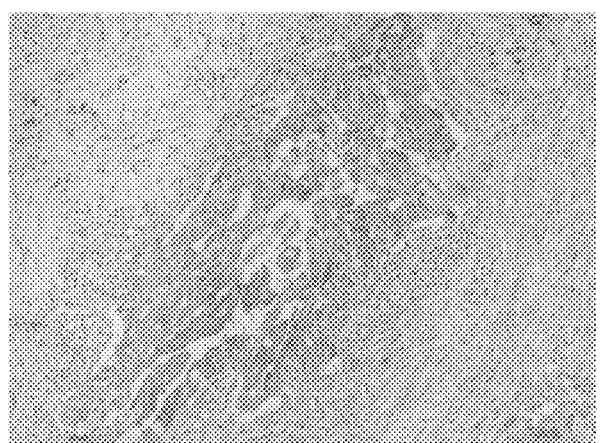
Figure 9:
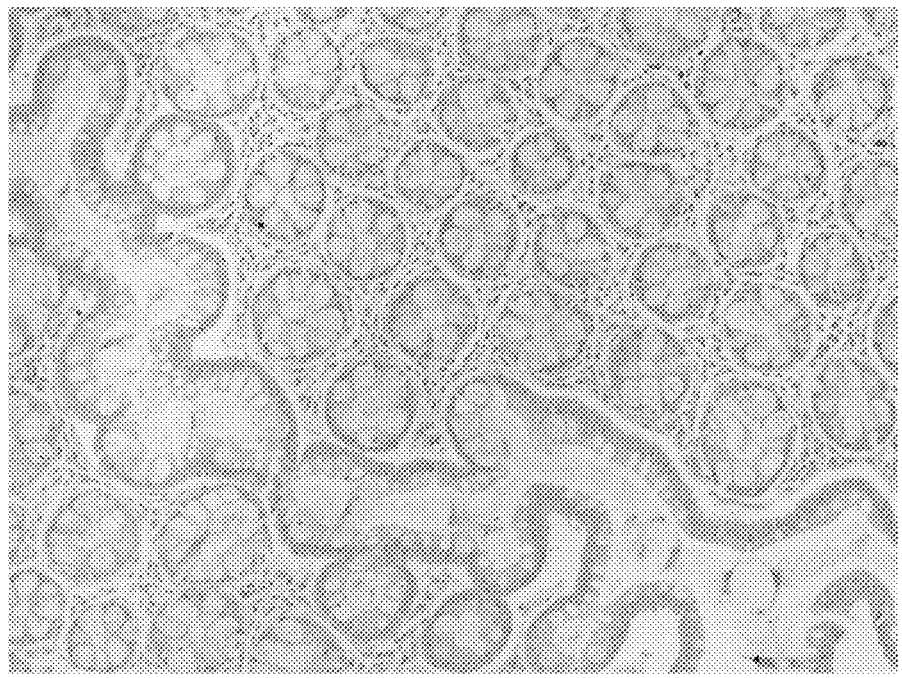

FIG. 7: Polyclonal Antibody K4344 (Pab K4344), Lung normal P1381-TN20, 200× magnification FIG. 7a: Pab K4344, lung normal P1381-TN20, 200× magnification FIG. 8: Pab K4344, Lung adenocarcinoma 725006.8, 200× magnification FIG. 8a: Pab K4344, Lung squamous carcinoma F060010, 200× magnification FIG. 8b: Pab K4344, Lung adenocarcinoma 725006.1, 200× magnification FIG. 9: Pab K4344, Colon normal F07-2538A3

Figure 9A:
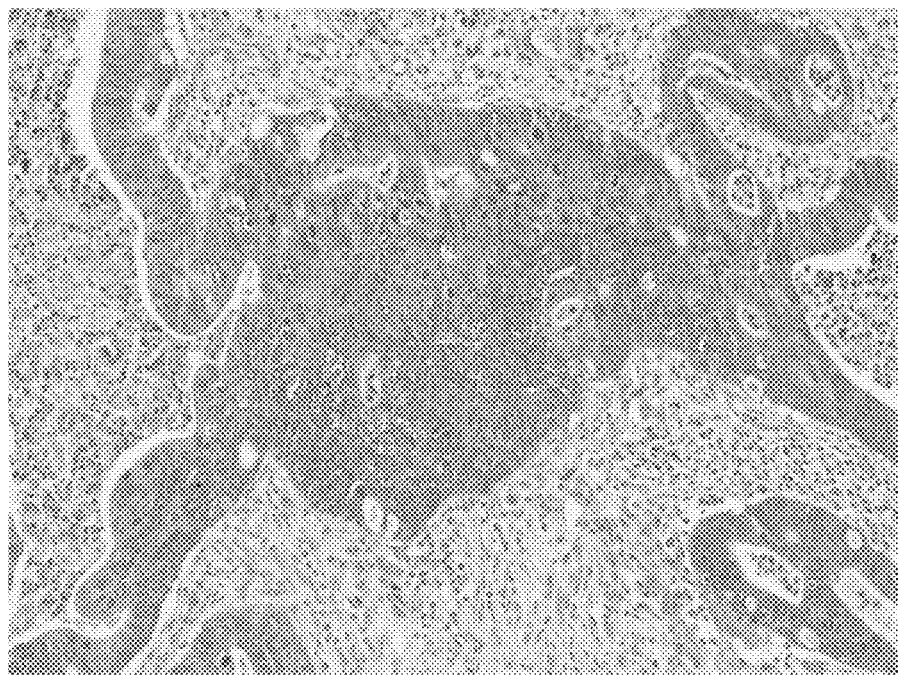

FIG. 9a: Pab K4344, Colon carcinoma F08-0978

Figure 10:
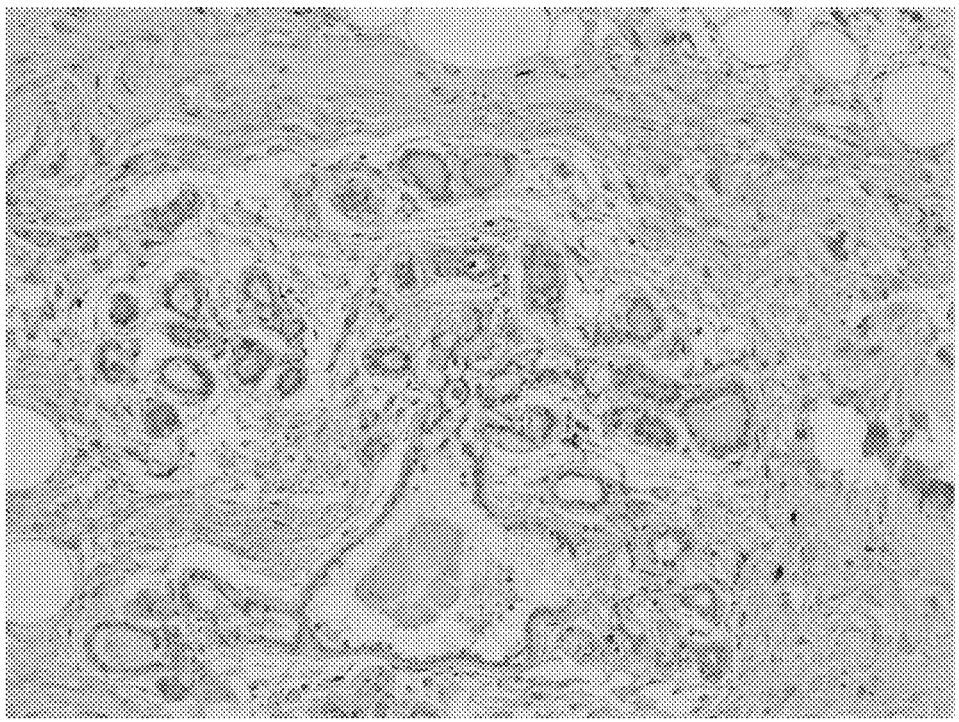

FIG. 10: Pab K4344, Breast normal 06-1143

Figure 10A:
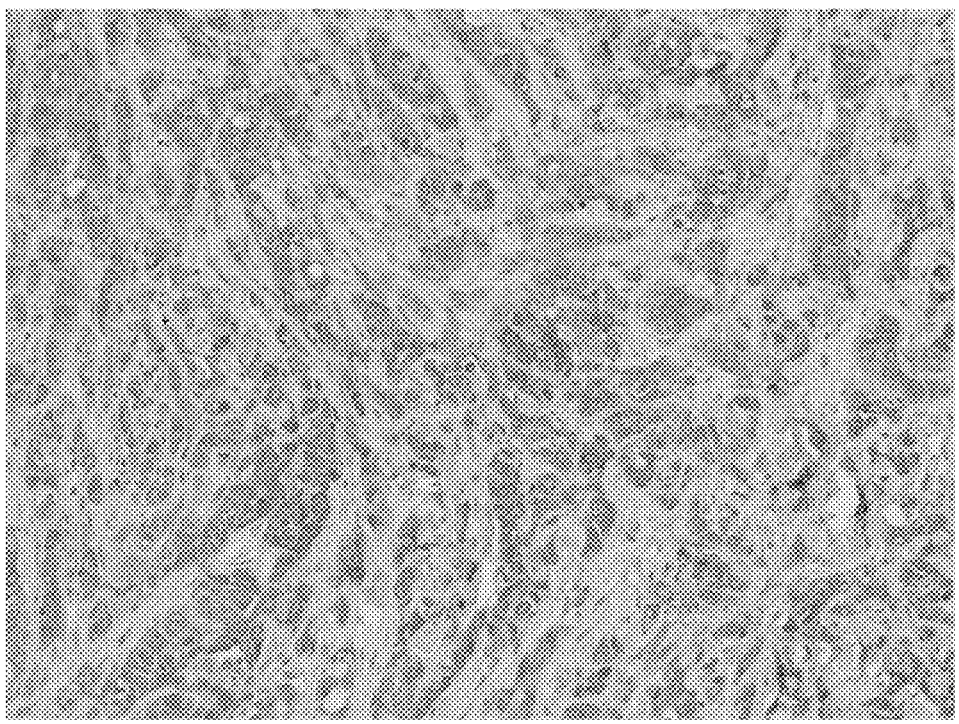

FIG. 10a: Pab K4344, Breast carcinoma 06-1786

Figure 11:
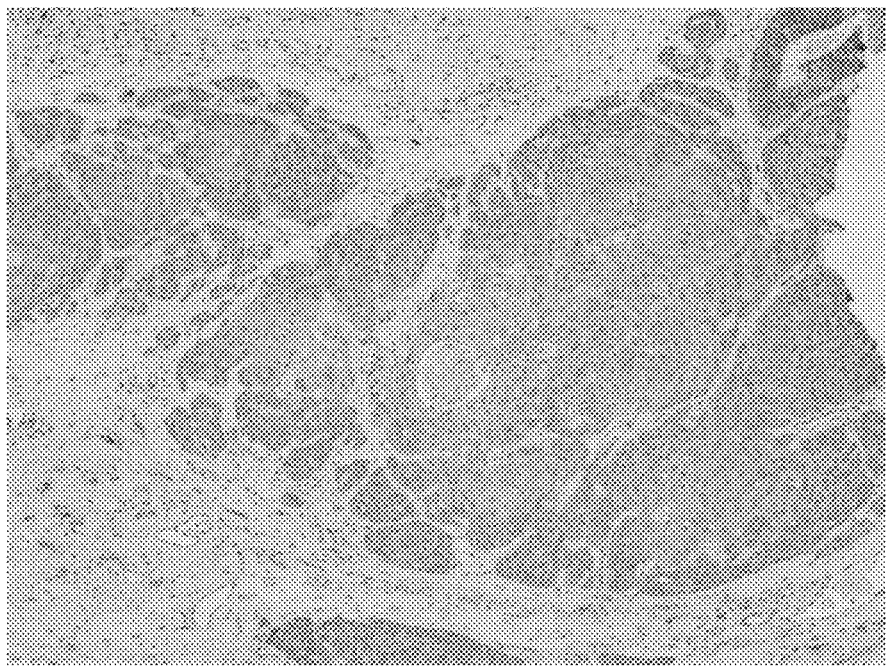

FIG. 11: Pab K4344, Larynx carcinoma (AST 292)

Figure 11A:
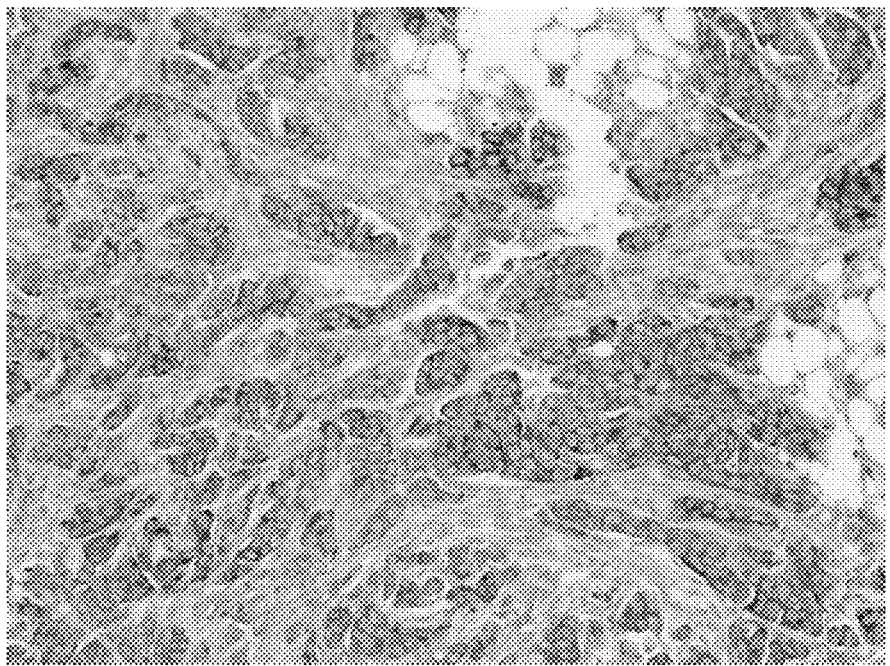

FIG. 11a: Pab K4344, Ovary carcinoma (TriStar 2n)

Figure 12:
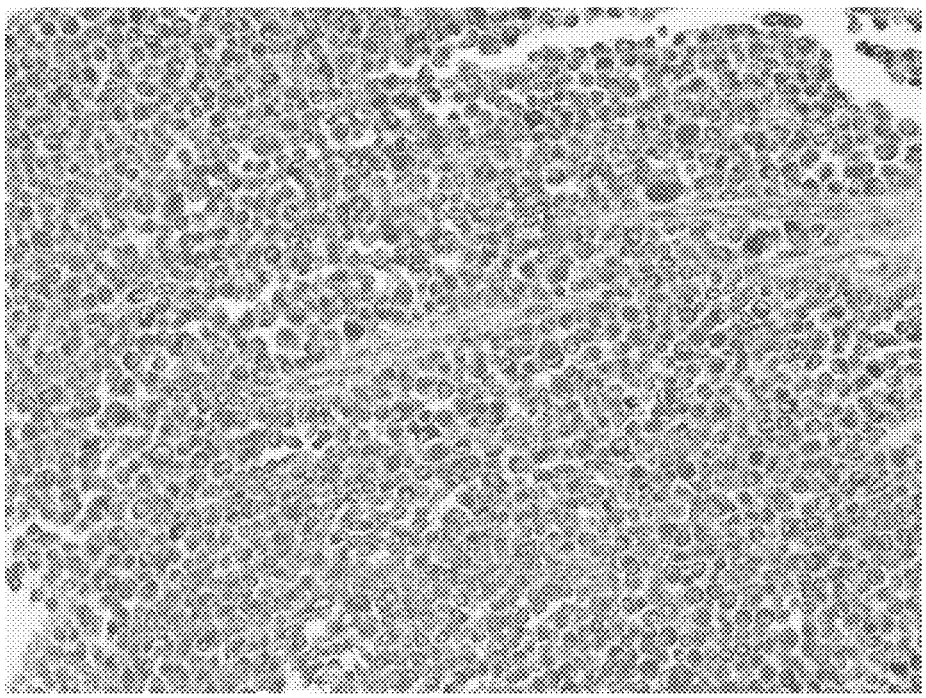

FIG. 12: Pab K4344, Melanoma (TriStar 4g)

Figure 12A:
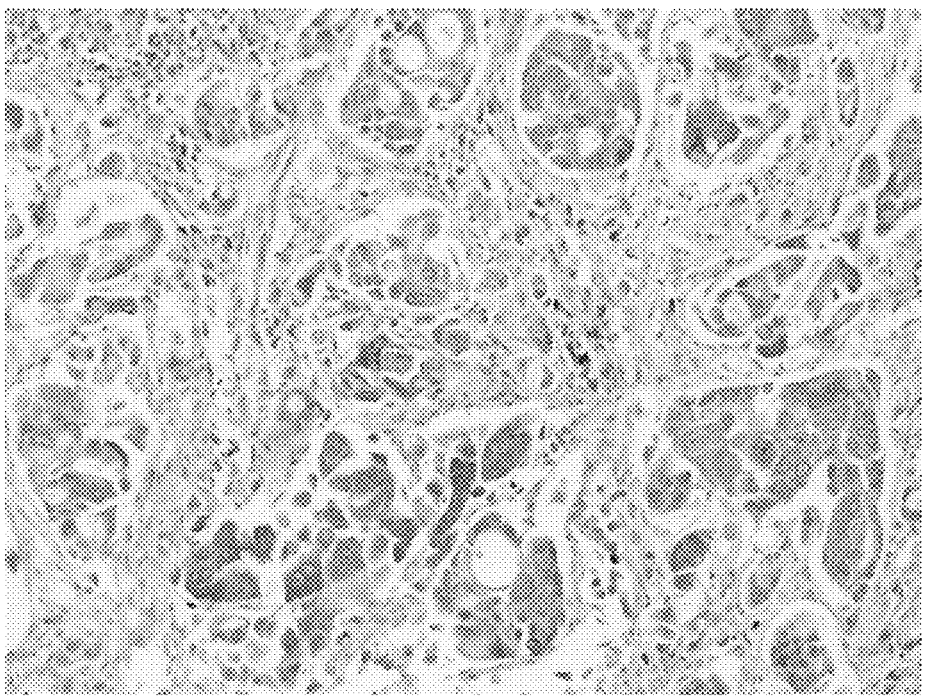

FIG. 12a: Pab K4344, Pancreas carcinoma (Tristar 5K)

DESCRIPTION OF THE SEQUENCES

SEQ ID NO: 1 shows the sequence according to FIG. 6. The human ARMET protein sequence (SwissProt database accession number: P55145).

SEQ ID NO: 2 shows a synthesized forward primer LC56for-EcoRI.

SEQ ID NO: 3 shows a synthesized reverse primer LC56rev-BamHI.

SEQ ID NO: 4 shows a synthesized peptide extension.

DETAILED DESCRIPTION OF THE INVENTION

The term "measurement" preferably comprises a qualitative, semi-qualitative or a quantitative measurement of an ARMET protein and/or fragments thereof in a sample. In a preferred embodiment the measurement is a semi-quantitative measurement, i.e. it is determined whether the concentration of ARMET is above or below a cut-off value. As the skilled artisan will appreciate, in a Yes- (presence) or No- (absence) assay, the assay sensitivity is usually set to match the cut-off value. A cut-off value can for example be determined from the testing of a group of healthy individuals. Preferably the cut-off is set to result in a specificity of 90%, also preferred the cut-off is set to result in a specificity of 95%, or also preferred the cut-off is set to result in a specificity of 98%. A value above the cut-off value can for example be indicative for the presence of cancer. In particular a value above the cut-off value can for example be indicative for the presence of lung, colon, breast, ovary, cervix, head and neck, endometrium, melanoma, bladder, kidney, pancreatic, prostate, esophagus, stomach and/or bile duct cancer. In a further preferred embodiment the measurement of ARMET is a quantitative measurement. In further embodiments the concentration of ARMET is correlated to an underlying diagnostic question like, e.g., stage of disease, disease progression, or response to therapy.

In another preferred embodiment, the cut-off is set to result in a sensitivity of 90%, also preferred the cut-off is set to result in a sensitivity of 95%, or also preferred the cut-off is set to result in a sensitivity of 98%.

A value below the cut-off value can for example be indicative for the absence of cancer. In particular a value below the cut-off value can for example be indicative for the absence of lung, colon, breast, ovary, cervix, head and neck, endometrium, melanoma, bladder, kidney, pancreatic, prostate, esophagus, stomach and/or bile duct cancer.

In a further preferred embodiment the measurement of ARMET is a quantitative measurement. In further embodiments the concentration of ARMET is correlated to an underlying diagnostic question like, e.g., stage of disease, disease progression, or response to therapy.

The biological role and function of ARMET (arginine-rich, mutated in early stage tumors, ARP, Swiss-PROT ID: P55145) protein remains largely elusive. The ARMET protein, characterized by the sequence given in SEQ ID NO:1 (FIG. 6), is a 20.3 kDa protein. The ARMET protein consists of 179 amino acids, and carries a predicted signal sequence (aa 1-21). The corresponding gene is located in chromosomal band 3p21.1 and was first characterized by Shridhar, V. et al. (Oncogene 12 (1996) 1931-1939). The gene is highly conserved and can be found many mammalian species, like rat, mouse, cow, and hamster. ARMET was named as such, because initial studies suggested ARMET to be 50 amino acids longer at the N-terminus carrying an arginine-rich region (Shridhar, V. et al., Oncogene 12 (1996) 1931-1939; Shridhar, R. et al., Cancer Res. 56 (1996) 5576-5578; Shridhar, V. et al., Oncogene 14 (1997) 2213-2216). However, more recent studies indicate transcribed evidence for a smaller open reading frame that does not encode the arginine tract (Tanaka, H. et al., Oncol. Rep. 7 (2000) 591-593; Mizobuchi, N. et al., Cell Struct. Funct. 32 (2007) 41-50). With the corresponding protein size correction, the initially described mutated codon ($ATG_{50}$) is now identified to be the initiation codon.

Early studies on the ARMET gene showed that a specific mutation ($ATG_{50} \rightarrow AGG$) was present in a certain subset of samples of many solid tumors, like renal cell carcinoma, non-small cell lung cancer, head and neck carcinoma, breast cancer, and pancreatic cancer (Shridhar, V. et al., Oncogene 12 (1996) 1931-1939; Shridhar, R. et al., Cancer Res. 56 (1996) 5576-5578; Shridhar, V. et al., Oncogene 14 (1997) 2213-2216). However, more recent studies suggest that there is no correlation between ARMET polymorphisms and pancreatic cancer (Piepoli, A. et al., World J. Gastroenterology 12 (2006) 6343-6348).

Petrova, P. et al. (J. Mol. Neurosci. 20 (2003) 173-188) purified the ARMET gene product from conditioned medium of a rat mesencephalic type-1 astrocyte cell line and named it MANF (Mensencephalic Astrocyte-dervied Neurotrophic Factor). Most recent studies demonstrated that ARMET is upregulated by the "unfolded protein response" (UPR), a process which is activated once misfolded proteins accumulate in the endoplasmatic reticulum (ER) (Tanaka, H. et al., Oncol. Rep. 7 (2000) 591-593; Apostolou, A. et al., Exp. Cell Res. 314 (2008) 2454-2467). Based on this study ARMET is characterized as a novel secreted mediator of the adaptive pathway of UPR.

Besides the studies on the mutation of $ATG_{50}$ no further studies connecting ARMET with the diagnosis or prognosis of cancer are found in the literature. Especially, tumor associated overexpression has not been reported yet, neither in transcriptional analysis nor in studies towards the presence of the protein.

As used herein, each of the following terms has the meaning associated with it in this section.

The articles "a" and "an" are used herein to refer to one or to more than one (i.e. to at least one) of the grammatical object of the article. By way of example, "a marker" means one marker or more than one marker. The term "at least" is used to indicate that optionally one or more further objects may be present. By way of example, a marker panel comprising at least (the markers) ARMET and CYFRA 21-1 may optionally comprise one or more other marker.

The expression "one or more" denotes 1 to 50, preferably 1 to 20 also preferred 2, 3, 4, 5, 6, 7, 8, 9, 10, 12, or 15.

The term "marker" or "biochemical marker" as used herein refers to a molecule to be used as a target for analyzing a patient's test sample. Examples of such molecular targets are proteins or polypeptides. Proteins or polypeptides used as a marker in the present invention are contemplated to include naturally occurring variants of said protein as well as fragments of said protein or said variant, in particular, immunologically detectable fragments. Immunologically detectable fragments preferably comprise at least 6, 7, 8, 10, 12, 15 or 20 contiguous amino acids of said marker polypeptide. One of skill in the art would recognize that proteins which are released by cells or present in the extracellular matrix may be damaged, e.g., during inflammation, and could become degraded or cleaved into such fragments. Certain markers are synthesized in an inactive form, which may be subsequently activated by proteolysis. As the skilled artisan will appreciate, proteins or fragments thereof may also be present as part of a complex. Such complex also may be used as a marker in the sense of the present invention. Variants of a marker polypeptide are encoded by the same gene, but may differ in their isoelectric point (=PI) or molecular weight (=MW), or both, e.g., as a result of alternative mRNA or pre-mRNA processing. The amino acid sequence of a variant is to 95% or more identical to the corresponding marker sequence. In addition, or in the alternative a marker polypeptide or a variant thereof may carry a post-translational modification. Non-limiting examples for posttranslational modifications are glycosylation, acylation, and/or phosphorylation.

ARMET

ARMET proteins, particularly soluble forms of ARMET proteins and/or fragments thereof, are detected in appropriate samples. Preferred samples are tissue samples or body fluids, such as blood, plasma, serum, sputum, urine, feces, bronchio-alveolar lavage (BAL), epithelial lining fluid (ELF) or sputum etc. Preferably, the sample is derived from a human subject, e.g., a tumor patient or a person in risk of a tumor or a person suspected of having a tumor. Also preferred ARMET is detected in a serum or plasma sample.

In a preferred embodiment according to the present invention, the concentration of a ARMET protein and/or fragments thereof is determined. In one embodiment, the marker ARMET is specifically measured from a sample by use of a specific binding agent.

A specific binding agent is, e.g., a receptor for ARMET, a lectin binding to ARMET or an antibody to ARMET. A specific binding agent has at least an affinity of $10^7$ l/mol for its corresponding target molecule. The specific binding agent preferably has an affinity of $10^8$ l/mol or also preferred of $10^9$ l/mol for its target molecule. As the skilled artisan will appreciate the term specific is used to indicate that other biomolecules present in the sample do not significantly bind to the binding agent specific for ARMET. Preferably, the level of binding to a biomolecule other than the target molecule results in a binding affinity which is at most only 10% or less, only 5% or less only 2% or less or only 1% or less of the affinity to the target molecule, respectively. A preferred specific binding agent will fulfil both the above minimum criteria for affinity as well as for specificity.

A specific binding agent preferably is an antibody reactive with ARMET. The term antibody refers to a polyclonal antibody, a monoclonal antibody, antigen binding fragments of such antibodies, single chain antibodies as well as to genetic constructs comprising the binding domain of an antibody.

Any antibody fragment retaining the above criteria of a specific binding agent can be used. Antibodies are generated by state of the art procedures, e.g., as described in Tijssen (Tijssen, P., Practice and theory of enzyme immunoassays, 11, Elsevier Science Publishers B.V., Amsterdam, the whole book, especially pages 43-78). In addition, the skilled artisan is well aware of methods based on immunosorbents that can be used for the specific isolation of antibodies. By these means the quality of polyclonal antibodies and hence their performance in immunoassays can be enhanced (Tijssen, P., supra, pages 108-115).

For the achievements as disclosed in the present invention polyclonal antibodies raised in rabbits may be used. However, clearly also polyclonal antibodies from different species, e.g., sheep or goat, as well as monoclonal antibodies can also be used. Since monoclonal antibodies can be produced in any amount required with constant properties, they represent ideal tools in development of an assay for clinical routine. The generation and the use of monoclonal antibodies to ARMET in a method according to the present invention, respectively, represent yet other preferred embodiments.

As the skilled artisan will appreciate now that ARMET has been identified as a marker which is useful in the assessment of cancer, preferably lung or colon cancer, various immuno-diagnostic procedures may be used to reach a result comparable to the achievements of the present invention. For example, alternative strategies to generate antibodies may be used. Such strategies comprise amongst others the use of synthetic peptides, representing an epitope of ARMET for immunization. Alternatively, DNA immunization also known as DNA vaccination may be used.

For measurement the sample obtained from an individual is incubated with the specific binding agent for ARMET under conditions appropriate for formation of a binding agent ARMET complex. Such conditions need not be specified, since the skilled artisan without any inventive effort can easily identify such appropriate incubation conditions. The amount of binding agent ARMET complex is measured and used in the assessment of cancer, preferably of lung cancer. As the skilled artisan will appreciate there are numerous methods to measure the amount of the specific binding agent ARMET complex all described in detail in relevant textbooks (cf., e.g., Tijssen P., supra, or Diamandis, E. P. and Christopoulos, T. K. (eds.), Immunoassay, Academic Press, Boston (1996)).

Preferably, ARMET is detected in a sandwich-type assay format. In such assay, a first specific binding agent is used to capture ARMET on the one side and a second specific binding agent, which is labeled to be directly or indirectly detectable, is used on the other side. The specific binding agents used in a sandwich-type assay format may be antibodies specifically directed against ARMET. The detection may be carried out by using different capturing and labeled antibodies, i.e. antibodies which recognize different epitopes on the ARMET protein.

A "marker of cancer" and in particular a "marker of lung cancer" and "marker of colon cancer" in the sense of the present invention is any marker that if combined with the marker ARMET adds relevant information in the assessment of cancer disease in the assessment of cancer in general or in the assessment of certain cancer types, e.g., in the assessment of LC or CRC. The information is considered relevant or of additive value if at a given specificity the sensitivity, or if at a given sensitivity the specificity, respectively, for the assessment of cancer can be improved by including said marker into a marker combination already comprising the marker ARMET. In the preferred embodiment of cancer assessment, the improvement in sensitivity or specificity, respectively, is statistically significant at a level of significance of $p=0.05$, 0.02, 0.01 or lower. Preferably, the one or more other tumor marker is selected from the group consisting of CYFRA 21-1, CEA, NSE, CA 19-9, CA 125, PSA, proGRP, SCC and NNMT.

The term "sample" as used herein refers to a biological sample obtained for the purpose of evaluation in vitro. In the methods of the present invention, the sample or patient sample preferably may comprise any body fluid. Preferred samples are whole blood, serum, plasma, bronchioalveolar lavage (BAL), epithelial lining fluid (ELF) or sputum, with plasma or serum being most preferred.

The term "tissue sample" and/or "tissue section" as used herein refers to a biological sample taken from a patient during surgery, therapeutic resections or a biopsy (e.g., incisional biopsy, excisional biopsy, core biopsy or needle aspiration biopsy) involving the removal of cells or tissues for the purpose of evaluation in vitro. When performing an analysis according to the present invention, the tissue sample material is used either directly or as a "tissue lysate". A "tissue sample" as used herein refers also to thin tissue slices usually accomplished through the use of a microtome. In any disclosed method embodiment involving a biological sample, such biological sample can be (but is not necessarily) mounted on a microscope slide, is a tissue section (such as a formalin-fixed and paraffin-embedded tissue section), and/or is a neoplastic tissue (such as, a lung cancer, colorectal cancer, head and neck cancer, gastric cancer, or glioblastoma).

A "tissue lysate", "cell lysate", "lysate", "lysed sample", "tissue extract" or "cell extract" as used herein refers to a sample and/or biological sample material comprising lysed tissue or cells, i.e. wherein the structural integrity of tissue or cells has been disrupted. To release the contents of cells or a tissue sample, the material is usually treated with enzymes and/or with chemicals to dissolve, degrade or disrupt the cellular walls and cellular membranes of such tissues or cells. The skilled artisan is fully familiar with appropriate methods for obtaining lysates. This process is encompassed by the term "lysis".

The term "assessing cancer" and in particular "assessing lung or colon cancer" is used to indicate that the method according to the present invention will (alone or together with other markers or variables, e.g., the criteria set forth by the UICC (see above)), e.g., aid the physician to establish or confirm the absence or presence of cancer, in particular of LC or of CRC or aid the physician in the prognosis, the detection of recurrence (follow-up of patients after surgery) and/or the monitoring of treatment, especially of chemotherapy.

As the skilled artisan will appreciate, any such assessment is made in vitro. The patient sample is discarded afterwards. The patient sample is solely used for the in vitro diagnostic method of the invention and the material of the patient sample is not transferred back into the patient's body. Typically, the sample is a liquid sample, e.g., whole blood, serum, or plasma.

Unless otherwise noted, technical terms are used according to conventional usage. Definitions of common terms in cell and molecular biology may be found in Lewin, B., Genes V, published by Oxford University Press (1994), ISBN 0-19-854287 9); Kendrew, J. et al. (eds.), The Encyclopedia of Molecular Biology, published by Blackwell Science Ltd. (1994), ISBN 0-632-02182-9); and Meyers, R. A. (ed.), Molecular Biology and Biotechnology: a Comprehensive Desk Reference, published by VCH Publishers, Inc. (1995), ISBN 1-56081-569 8).

In a preferred embodiment the present invention relates to a method for assessing cancer, e.g., LC, in vitro by biochemical markers, comprising measuring in a sample the concentration of ARMET protein and/or fragments thereof and using the concentration determined in the assessment of cancer, e.g., LC.

In another preferred embodiment the present invention relates to a method for assessing LC in vitro by biochemical markers, comprising measuring in a sample the concentration of ARMET protein and/or fragments thereof and using the concentration determined in the assessment of LC.

The inventors of the present invention have surprisingly been able to detect an increased concentration of the marker ARMET in a significant percentage of samples derived from patients with cancer, in particular with lung, colon, breast, ovary, cervix, head and neck, endometrium, melanoma, bladder, kidney, pancreatic, prostate, esophagus, stomach or bile duct cancer. Even more surprising they have been able to demonstrate that the increased concentration of ARMET in such sample obtained from an individual can be used in the assessment of cancer, in particular of the above-mentioned cancer diseases.

The ideal scenario for diagnosis would be a situation wherein a single event or process would cause the respective disease as, e.g., in infectious diseases. In all other cases correct diagnosis can be very difficult, especially when the etiology of the disease is not fully understood as is the case for many cancer types, e.g., for LC. As the skilled artisan will appreciate, no biochemical marker is diagnostic with 100% specificity and at the same time 100% sensitivity for a given multifactorial disease, for example for LC. Rather, biochemical markers, e.g., CYFRA 21-1, CEA, CA 125, proGRP.SCC, or as shown here ARMET can be used to assess with a certain likelihood or predictive value, e.g., the presence, absence, or the severity of a disease. Therefore in routine clinical diagnosis, generally various clinical symptoms and biological markers are considered together in the diagnosis, treatment and management of the underlying disease.

Biochemical markers can either be determined individually or in a preferred embodiment of the invention they can be measured simultaneously using a chip or a bead based array technology. The concentrations of the biomarkers are then either interpreted independently, e.g., using an individual cut-off for each marker, or they are combined for interpretation.

In a further preferred embodiment the assessment of cancer according to the present invention is performed in a method comprising measuring in a sample the concentration of a) an ARMET protein and/or fragments thereof, b) one or more other marker of cancer, and c) using the measurement result, e.g., the concentration determined in step (a) and step (b), respectively, in the assessment of cancer.

In the assessment of cancer the marker ARMET will be of advantage in one or more of the following aspects: screening; diagnostic aid; prognosis; monitoring of therapy such as chemotherapy, radiotherapy, and immunotherapy.

Screening

Screening is defined as the systematic application of a test to identify individuals, e.g., at risk individuals, for indicators of a disease, e.g., the presence of cancer. Preferably the screening population is composed of individuals known to be at higher than average risk of cancer. For example, a screening population for lung cancer is composed of individuals known to be at higher than average risk of lung cancer, like smokers, ex-smokers, and uranium-, quartz- or asbestos-exposed workers.

In the preferred embodiment, a tissue sample or any body fluid such as plasma, serum, stool, urine, sputum, bronchio-alveolar lavage (BAL) or epithelial lining fluid (ELF), is used as a sample in the screening for cancer, e.g., lung cancer.

In another preferred embodiment of LC, sputum is used as a sample in the screening for lung cancer.

For many diseases, no single biochemical marker in the circulation will ever meet the sensitivity and specificity criteria required for screening purposes. This appears to be also true for cancer and in particular for lung cancer. It has to be expected that a marker panel comprising a plurality of markers will have to be used in cancer screening. The data established in the present invention indicate that the marker ARMET will form an integral part of a marker panel appropriate for screening purposes. The present invention therefore relates to the use of ARMET as one marker of a cancer marker panel, i.e. a marker panel comprising ARMET and one or more additional marker for cancer screening purposes. In particular, the present invention relates to the use of ARMET as one marker of a general cancer marker panel. Such marker panel comprises the marker ARMET and one or more additional markers, e.g., general cancer markers and/or markers for the above-mentioned type of cancer.

ARMET is also likely to contribute to marker panels for certain specific types of cancer, e.g., lung, colon, breast, ovary, cervix, head and neck, endometrium, melanoma, bladder, kidney, pancreatic, prostate, esophagus, stomach and/or bile duct cancer.

Other preferred types of cancer to be assessed with a marker panel comprising ARMET are lung, colon, breast, ovary, cervix, head and neck, endometrium, melanoma, bladder, kidney, pancreatic, prostate, esophagus, stomach or bile duct cancer.

Other preferred types of cancer to be assessed with a marker panel comprising ARMET are lung, colon, breast, ovary, cervix, head and neck, endometrium, melanoma, bladder, kidney, pancreatic or prostate cancer.

Other preferred types of cancer to be assessed with a marker panel comprising ARMET are lung, colon, breast, ovary, cervix, head and neck, endometrium or melanoma cancer.

Other preferred types of cancer to be assessed with a marker panel comprising ARMET are lung, colon, breast, cervix, endometrium or ovary cancer.

Other preferred types of cancer to be assessed with a marker panel comprising ARMET are lung, colon, breast or ovary cancer.

Other preferred types of cancer to be assessed with a marker panel comprising ARMET are lung cancer (LC) or colorectal cancer (CRC).

A preferred type of cancer to be assessed with a marker panel comprising ARMET is lung cancer (LC).

A preferred type of cancer to be assessed with a marker panel comprising ARMET is colon cancer (CRC).

The present data further indicate that certain combinations of markers will be advantageous in the screening for cancer. For example, with reference to the preferred embodiment of screening LC or CRC, the present invention also relates to the use of a marker panel comprising ARMET and CYFRA 21-1, or of a marker panel comprising ARMET and CEA, or of a marker panel comprising ARMET and NSE, or of a marker panel comprising ARMET and CA 19-9, or of a marker panel comprising ARMET and CA 125, or of a marker panel comprising ARMET and PSA, or of a marker panel comprising ARMET and proGRP, or of a marker panel comprising ARMET and SCC, or of a marker panel comprising ARMET and NNMT, or of a marker panel comprising ARMET and two or more markers selected from the group consisting of CYFRA 21-1, CEA, NSE, CA 19-9, CA 125, PSA, proGRP, SCC and/or NNMT.

Diagnostic Aid

Markers may either aid the differential diagnosis of benign vs. malignant disease in a particular organ, help to distinguish between different histological types of a tumor, or to establish baseline marker values before surgery.

Today, important methods used in the detection of lung cancer are radiology and/or computed tomography (CT) scans. Small nodules, i.e. small regions of suspect tissue can be visualized by these methods. However, many of these nodules—more than 90% with CT—represent benign tissues changes, and only a minority of nodules represents cancerous tissue. Use of the marker ARMET may aid in the differentiation of benign versus malign disease.

In a preferred embodiment the marker ARMET is used in an immunohistological method in order to establish or confirm different histological types of lung, colon, breast, ovary, cervix, head and neck, endometrium, melanoma, bladder, kidney, pancreatic, prostate, esophagus, stomach and/or bile duct cancer, preferably LC.

Since ARMET as a single marker might be superior to other markers, e.g., in the case of LC to other markers, like CEA or NSE, it has to be expected that ARMET will be used as a diagnostic aid, especially by establishing a baseline value before surgery. The present invention thus also relates to the use of ARMET for establishing a baseline value before surgery for cancer.

Prognosis

Prognostic indicators can be defined as clinical, pathological, or biochemical features of cancer patients and their tumors that predict with a certain likelihood the disease outcome. Their main use is to help to rationally plan patient management, i.e. to avoid undertreatment of aggressive disease and overtreatment of indolent disease, respectively. Molina, R. et al., Tumor Biol. 24 (2003) 209-218 evaluated the prognostic value of CEA, CA 125, CYFRA 21-1, SSC and NSE in NSCLC. In their study abnormal serum levels of the markers NSE, CEA, and LDH (lactate dehydrogenase) appeared to indicate shorter survival.

As ARMET alone significantly contributes to the differentiation of cancer patients, e.g., LC or CRC patients, from healthy controls, it has to be expected that it will aid in assessing the prognosis of patients suffering from cancer, preferably from LC or CRC. The level of preoperative ARMET will most likely be combined with one or more other marker for cancer and/or the TNM staging system. In a preferred embodiment ARMET is used in the prognosis of patients with LC or CRC.

Monitoring of Chemotherapy

Merle, P. et al., Int. J. of Biological Markers 19 (2004) 310-315 have evaluated CYFRA 21-1 serum level variations in patients with locally advanced NSCLC treated with induction chemotherapy. They conclude that early monitoring of CYFRA 21-1 serum levels may be a useful prognostic tool for tumor response and survival in stage III NSCLC patients. In addition, reports have described the use of CEA in monitoring the treatment of patients with LC (Fukasawa, T. et al., Cancer & Chemotherapy 13 (1986) 1862-1867) Most of these were retrospective, non-randomized and contained small numbers of patients. As in the case of the studies with CYFRA 21-1 the CEA studies suggested: a) that patients with a decrease in CEA levels while receiving chemotherapy generally had a better outcome than those patients whose CEA levels failed to decrease and (b) for almost all patients, increases in CEA levels were associated with disease progression.

It is expected that ARMET will be at least as good a marker for monitoring of chemotherapy as CYFRA 21-1 or CEA, respectively. The present invention therefore also relates to the use of ARMET in the monitoring of cancer patients and preferably of lung cancer (LC) or colon cancer (CRC) patients under chemotherapy. In the monitoring of therapy in one preferred embodiment the measurements for ARMET and for at least one marker selected from the group consisting of CYFRA 21-1, CEA, NSE, CA 19-9, CA 125, PSA, proGRP, SCC and/or NNMT will be combined and used in the assessment of lung (LC) cancer.

Follow-Up

A large portion of LC patients who undergo surgical resection aimed at complete removal of cancerous tissue, later develop recurrent or metastatic disease (Wagner, H. Jr., Chest 117 (2000) S110-S118; Buccheri, G. et al., Ann. Thorac. Surg. 75 (2003) 973-980). Most of these relapses occur within the first 2-3 years after surgery. Since recurrent/metastatic disease is invariably fatal if detected too late, considerable research has focused on cancer relapse at an early and thus potentially treatable stage.

Consequently, many cancer patients, e.g., LC patients undergo a postoperative surveillance program which frequently includes regular monitoring with CEA. Serial monitoring with CEA one year after surgical resection has been shown to detect an early postoperative recurrent/metastatic disease with a sensitivity of approximately 29%, at a specificity of approximately 97%, even in the absence of suspicious symptoms or signs (Buccheri, G. et al., Ann. Thorac. Surg. 75 (2003) 973-980). Thus, the follow-up of patients with LC after surgery is one of the most important fields of use for an appropriate biochemical marker. Due to the high sensitivity of ARMET in the LC patients investigated it is likely that ARMET alone or in combination with one or more other marker will be of great help in the follow-up of LC patients, especially in LC patients after surgery. The use of a marker panel comprising ARMET and one or more other marker of LC in the follow-up of LC patients represents a further preferred embodiment of the present invention.

The present invention in a preferred embodiment relates to the use of ARMET in the diagnostic field of cancer. Preferably ARMET is used in the assessment of lung, colon, breast, ovary, cervix, head and neck, endometrium, melanoma, bladder, kidney, pancreas, prostate, esophagus, stomach or bile duct cancer, respectively.

In yet a further preferred embodiment the present invention relates to the use of ARMET as a marker molecule for cancer, e.g., for cancer in general or for specific types of cancer, such as lung, colon, esophagus, head and neck, stomach, bile duct, pancreas, kidney, cervix, ovary, breast, bladder, endometrium or prostate cancer in combination with one or more further marker molecules for cancer. The further marker molecules may be cancer-type unspecific general marker molecules and/or cancer-type specific marker molecules, e.g., marker molecules for lung or colon cancer. ARMET and the at least one further marker are used in the assessment of cancer, e.g., lung or colon cancer in a liquid sample obtained from an individual. Preferred selected other cancer markers with which the measurement of ARMET may be combined are Cyfra 21-1, CEA, NSE, CA 125, CA 19-9, PSA, proGRP, SCC and NNMT. In particular, preferred selected other LC markers with which the measurement of ARMET may be combined are CYFRA 21-1, CEA, CA 19-9, SCC, CA 125, proGRP and/or NSE. Yet further preferred the marker panel used in the assessment of cancer, e.g., LC comprises ARMET and at least one other marker molecule selected from the group consisting of CYFRA 21-1 and CEA.

As the skilled artisan will appreciate there are many ways to use the measurements of two or more markers in order to improve the diagnostic question under investigation. In a quite simple, but nonetheless often effective approach, a positive result is assumed if a sample is positive for at least one of the markers investigated. This may, e.g., the case when diagnosing an infectious disease, like AIDS.

Frequently, however, the combination of markers is evaluated. Preferably the values measured for markers of a marker panel, e.g., for ARMET and CYFRA 21-1, are mathematically combined and the combined value is correlated to the underlying diagnostic question. Marker values may be combined by any appropriate state of the art mathematical method. Well-known mathematical methods for correlating a marker combination to a disease employ methods like, discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. The skilled artisan will have no problem in selecting an appropriate method to evaluate a marker combination of the present invention. Preferably the method used in correlating the marker combination of the invention, e.g., to the absence or presence of LC is selected from DA (i.e. Linear-, Quadratic-, Regularized Discriminant Analysis), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting Methods), or Generalized Linear Models (i.e. Logistic Regression). Details relating to these statistical methods are found in the following references: Ruczinski, I., et al, J. of Computational and Graphical Statistics, 12 (2003) 475-511; Friedman, J. H., J. of the American Statistical Association 84 (1989) 165-175; Hastie, T. et al., The Elements of Statistical Learning, Springer Series in Statistics (2001); Breiman, L., et al., Classification and regression trees, California: Wadsworth (1984); Breiman, L., Random Forests, Machine Learning, 45 (2001) 5-32; Pepe, M. S., The Statistical Evaluation of Medical Tests for Classification and Prediction, Oxford Statistical Science Series, 28 (2003); and Duda, R. O. et al., Pattern Classification, Wiley Interscience, 2nd edition (2001).

It is a preferred embodiment of the invention to use an optimized multivariate cut-off for the underlying combination of biological markers and to discriminate state A from state B, e.g., diseased from healthy. In this type of analysis the markers are no longer independent but form a marker panel.

Accuracy of a diagnostic method is best described by its receiver-operating characteristics (ROC) (see especially Zweig, M. H., and Campbell, G., Clin. Chem. 39 (1993) 561-577). The ROC graph is a plot of all of the sensitivity/ specificity pairs resulting from continuously varying the decision thresh-hold over the entire range of data observed.

The clinical performance of a laboratory test depends on its diagnostic accuracy, or the ability to correctly classify subjects into clinically relevant subgroups. Diagnostic accuracy measures the test's ability to correctly distinguish two different conditions of the subjects investigated. Such conditions are for example health and disease or benign versus malignant disease.

In each case, the ROC plot depicts the overlap between the two distributions by plotting the sensitivity versus 1-specificity for the complete range of decision thresholds. On the y-axis is sensitivity, or the true-positive fraction [defined as (number of true-positive test results)/(number of true-positive+number of false-negative test results)]. This has also been referred to as positivity in the presence of a disease or condition. It is calculated solely from the affected subgroup. On the x-axis is the false-positive fraction, or 1-specificity [defined as (number of false-positive results)/(number of true-negative+number of false-positive results)]. It is an index of specificity and is calculated entirely from the unaffected subgroup. Because the true- and false-positive fractions are calculated entirely separately, by using the test results from two different subgroups, the ROC plot is independent of the prevalence of disease in the sample. Each point on the ROC plot represents a sensitivity/1-specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. (If the ROC plot falls completely below the 45° diagonal, this is easily remedied by reversing the criterion for "positivity" from "greater than" to "less than" or vice versa.) Qualitatively, the closer the plot is to the upper left corner, the higher the overall accuracy of the test.

One preferred way to quantify the diagnostic accuracy of a laboratory test is to express its performance by a single number. Such an overall parameter, e.g., is the so-called "total error" or alternatively the "area under the curve=AUC". The most common global measure is the area under the ROC plot. By convention, this area is always ≥0.5 (if it is not, one can reverse the decision rule to make it so). Values range between 1.0 (perfect separation of the test values of the two groups) and 0.5 (no apparent distributional difference between the two groups of test values). The area does not depend only on a particular portion of the plot such as the point closest to the diagonal or the sensitivity at 90% specificity, but on the entire plot. This is a quantitative, descriptive expression of how close the ROC plot is to the perfect one (area=1.0).

Combining measurements of ARMET with other markers like CYFRA 21-1 or CEA, or with other markers of LC yet to be discovered, ARMET leads and will lead, respectively, to further improvements in assessment of LC.

In a preferred embodiment the present invention relates to a method for improving the diagnostic accuracy for cancer, e.g., LC versus healthy controls by measuring in a sample the concentration of at least ARMET and CYFRA 21-1, and optionally of CEA, NSE, CA 19-9, CA 125, PSA, proGRP, SCC and/or NNMT, respectively and correlating the concentrations determined to the presence or absence of cancer, e.g., LC, the improvement resulting in more patients being correctly classified as suffering from cancer, e.g., LC versus healthy controls as compared to a classification based on any single marker investigated alone.

In a preferred method according to the present invention at least the concentration of the biomarkers ARMET and CYFRA 21-1, respectively, is determined and the marker combination is used in the assessment of cancer, e.g., LC.

In a further preferred method according to the present invention at least the concentration of the biomarkers ARMET and CEA, respectively, is determined and the marker combination is used in the assessment of cancer, e.g., LC.

In a further preferred method according to the present invention at least the concentration of the biomarkers ARMET and NSE, respectively, is determined and the marker combination is used in the assessment of cancer, e.g., LC.

In a further preferred method according to the present invention at least the concentration of the biomarkers ARMET and CA 19-9, respectively, is determined and the marker combination is used in the assessment of cancer, e.g., LC.

In a further preferred method according to the present invention at least the concentration of the biomarkers ARMET and CA 125, respectively, is determined and the marker combination is used in the assessment of cancer, e.g., LC.

In a further preferred method according to the present invention at least the concentration of the biomarkers ARMET and PSA, respectively, is determined and the marker combination is used in the assessment of cancer, e.g., LC.

In a further preferred method according to the present invention at least the concentration of the biomarkers ARMET and proGRP, respectively, is determined and the marker combination is used in the assessment of cancer, e.g., LC.

In a further preferred method according to the present invention at least the concentration of the biomarkers ARMET and SCC, respectively, is determined and the marker combination is used in the assessment of cancer, e.g., LC.

In a further preferred method according to the present invention at least the concentration of the biomarkers ARMET and NNMT, respectively, is determined and the marker combination is used in the assessment of cancer, e.g., LC.

In yet a further preferred method according to the present invention at least the concentration of the biomarkers ARMET, CYFRA 21-1, and CEA, respectively, is determined and the marker combination is used in the assessment of cancer, e.g., LC.

In yet a further preferred method according to the present invention at least the concentration of the biomarkers ARMET, CYFRA 21-1, and NSE, respectively, is determined and the marker combination is used in the assessment of cancer, e.g., LC.

In yet a further preferred method according to the present invention at least the concentration of the biomarkers ARMET, CYFRA 21-1, and CA 19-9, respectively, is determined and the marker combination is used in the assessment of cancer, e.g., LC.

In yet a further preferred method according to the present invention at least the concentration of the biomarkers ARMET, CYFRA 21-1, and CA 125, respectively, is determined and the marker combination is used in the assessment of cancer, e.g., LC.

In yet a further preferred method according to the present invention at least the concentration of the biomarkers ARMET, CYFRA 21-1, and PSA, respectively, is determined and the marker combination is used in the assessment of cancer, e.g., LC.

In yet a further preferred method according to the present invention at least the concentration of the biomarkers ARMET, CYFRA 21-1, and proGRP, respectively, is determined and the marker combination is used in the assessment of cancer, e.g., LC.

In yet a further preferred method according to the present invention at least the concentration of the biomarkers ARMET, CYFRA 21-1, and SCC, respectively, is determined and the marker combination is used in the assessment of cancer, e.g., LC.

In yet a further preferred method according to the present invention at least the concentration of the biomarkers ARMET, CYFRA 21-1, and NNMT, respectively, is determined and the marker combination is used in the assessment of cancer, e.g., LC.

The following examples, sequence listing and the figures are provided to aid the understanding of the present invention, the true scope of which is set forth in the appended claims. It is understood that modifications can be made in the procedures set forth without departing from the spirit of the invention.

Example 1

Identification of ARMET as a Potential Marker for Lung Cancer

Sources of Tissue:

In order to identify tumor-specific proteins as potential diagnostic markers for lung cancer, analysis of two different kinds of tissue using proteomics methods is performed.

In total, tissue specimen from 11 patients suffering from lung cancer (LC) are analyzed. From each patient two different tissue types are collected from therapeutic resections: tumor tissue (>80% tumor) (T) and adjacent healthy tissue (N) The latter one serves as matched healthy control samples. Tissues are immediately snap frozen after resection and stored at −80° C. before processing. Tumors are diagnosed by histopathological criteria.

Tissue Preparation:

0.8-1.2 g of frozen tissue are cut into small pieces, transferred to the chilled grinding jar of a mixer ball mill and completely frozen by liquid nitrogen. The tissue is pulverized in the ball mill, dissolved in the 10-fold volume (w/v) of lysis buffer (40 mM Na-citrate, 5 mM $MgCl_2$, 1% Genapol X-080, 0.02% Na-azide, Complete® EDTA-free [Roche Diagnostics GmbH, Mannheim, Germany, Cat. No. 1 873 580]) and subsequently homogenized in a Wheaton glass homogenizer (20× loose fitting, 20× tight fitting). The homogenate is subjected to centrifugation (10' at 5,000×g), the supernatant is transferred to another vial and again subjected to centrifugation (15' at 20,000×g). The resulting supernatant contains the soluble proteins and is used for further analysis.

Sample Preparation for LC-ESI-MSMS-Analysis:

The protein concentration of the soluble protein fraction is determined using the Bradford assay. 400 µg of each sample are diluted with Laemmli sample buffer to a concentration of 2 mg/ml and incubated at 95° C. for 10 min. Gel electrophoresis (3×120 µg per sample, BioRad 10-20% Tris-HCl, 16×16 cm) was performed following the BioRad instructions manual for 'large precast gels' (30 min-25 mA, 2.5 h-35 mA). After protein separation the gel is incubated with 50% methanol/10% acetic acid for 30 min at room temperature following 1 h incubation with 20 mM DTT/100 mM $NH_4HCO_3$ for reduction and 2 h with 100 mM iodine acetamide/100 mM $NH_4HCO_3$ for alkylation. Staining of the gel is carried out over night at room temperature with 20% methanol/20% Coomasie blue (Novex staining kit).

The region between 6 and 31 kDa as indicated by marker proteins is cut out and sliced into pieces of 1 mm size. Complete destaining of the gel is achieved by incubating with 0.1 M $NH_4HCO_3$/30% acetonitrile. After washing with water the gel pieces are dried in a speedvac at 45° C. and 10 mbar. The digest with trypsin (Proteomics grade, Roche Diagnostics GmbH) is done over night at room temperature followed by extraction with 35% acetonitrile/0.1% formic acid. The extraction solution is evaporated in a speedvac and the sample resolved in 100 µl 5% acetonitrile/0.5% acetic acid/0.1% formic acid.

LC-ESI-MSMS-Analysis:

The tryptic digest (100 µl) is separated by two-dimensional HPLC (MudPIT) on a Nano-LC system (Ultimate, Famos, Switchos; LC Packings, Idstein, Germany). The separation is performed with self packed two-dimensional columns (Fused silica: PicoFrit 75 µm, New Objective; RP: ProntoSil 120-5-C18 AQ+, Bischoff; SCX: Partisil 10, Whatman). 11 SCX fractions are generated by step elution with successively increasing amounts of $NH_4Ac$ (0 to 1500 mM). They are further separated on the RP part of the column and online analyzed using data dependent scans with an ESI-MS ion trap (LCQ deca XP; Thermo Electron, Massachusetts, USA; see Table 1 for parameters). For each sample three runs are performed. The raw data are processed with a non-commercial Roche own data managing system using Sequest as base algorithm (Parameters see Table 1). The resulting lists of identified peptides and proteins from replicate runs where combined.

The protein ARMET is identified by aid of the sequences identified and given in Table 2.

Detection of ARMET as a Potential Marker for Lung Cancer:

For each patient the identified proteins and the number of corresponding peptides from the tumor sample are compared to the accordant results from adjacent normal tissue. By this means, protein ARMET is found to be specifically present or to be strongly abundant in tumor tissue and not to be detectable or to be barely detectable in healthy control tissue.

TABLE 1

MSMS-data acquisition and database search parameters

| MSMS-data acquisition | MS exclusion | 350-2000 Da for precursor ions |
|---|---|---|
| | Repeat count | 2 |
| | Repeat duration | 0.25 min |

TABLE 1-continued

MSMS-data acquisition and database search parameters

| MSMS-data acquisition | MS exclusion | 350-2000 Da for precursor ions |
|---|---|---|
| | Exclusion list size | 50 |
| | Exclusion duration | 5 min |
| | Exclusion mass width | low 0.5 Da, high 1.5 Da |
| Sequest | Number of ions | 30 |
| | Minimal ion intensity | 10.000 counts |
| | Precursor mass tolerance | 1.5 Da |
| | Fragment mass tolerance | 1.5 Da |
| | $X_{corr}$ | >1.8; 2.3, 2.8 (z = 1; 2; 3) |
| | dCn | >0.1 |
| | Sp | >500 |
| Databases | | Humangp (assembled by Roche Bioinformatics) |

The protein ARMET is strongly over-represented in tumor tissue from patients suffering from lung cancer. The following peptide sequences of the protein ARMET are identified by database search form LCQ-MS²-data in tumor tissue:

The following sequences derived from ARMET are identified using the above described method.

TABLE 2

Sequences identified by ESI-MSMS

| sequence identified | stretch of amino acids from ARMET (cf. SEQ ID NO: 1) |
|---|---|
| DRDVTFSPATIENELIK | 43-59 |
| DVTFSPATIENELIK | 45-59 |
| IINEVSKPLAHHIPVEK | 85-101 |
| LCYYIGATDDAATK | 71-84 |
| QIDLSTVDLK | 121-130 |

Example 2

Generation of Antibodies to the Cancer Marker Protein ARMET

Polyclonal antibody to the lung cancer marker protein ARMET is generated for further use of the antibody in the measurement of serum and plasma and blood levels of ARMET by immunodetection assays, e.g., Western Blotting and ELISA.

Recombinant Protein Expression in *E. coli*:

In order to generate antibodies against ARMET, the recombinant antigen is produced in *E. coli*: Therefore, the ARMET coding region is PCR amplified from the full-length cDNA clone IRAUp969D0638D obtained from the German Resource Center for Genome Research (RZPD, Berlin, Germany) using the primers:

Forward primer LC56for-EcoRI:
5' acgtacgt<u>gaattc</u>attaaagaggagaaattaactatATGAGAGGA

TCGCATCACCATCACCATCACATTGAAGGCCGTAGGAGGATGTGGGCCA

CGCAG
(SEQ ID NO: 2/EcoRI site underlined, coding nucleotides in capital letters), Reverse primer LC56rev-BamHI:
5' acgtacgt<u>ggatcc</u>tcattaCAAATCGGTCCGTGCACTGG
(SEQ ID NO: 3/BamHI site underlined, coding nucleotides in capital letters).

The forward primer features (besides the EcoRI cloning and ribosomal binding sites) oligonucleotides coding for an N-terminal MRGSHHHHHHIEGR peptide extension (SEQ ID NO: 4) introduced in-frame to the ARMET protein. The EcoRI/BamHI digested PCR fragment is ligated into the corresponding pQE-30 (Qiagen, Hilden, Germany) vector fragment which is subsequently transformed into *E. coli* XL1-blue competent cells. After sequence analysis, the plasmid is transformed into *E. coli* BL21 competent cells for expression under the IPTG-inducible T5 promoter of the pQE vector series following the manufacturer's instructions.

For purification of the MRGSHHHHHHIEGR-ARMET fusion protein ("MRGSHHHHHHIEGR" disclosed as SEQ ID NO: 4), 1 L of an over-night induced bacterial culture is pelleted by centrifugation and the cell pellet is lysed by resuspension in 100 mM sodium-phosphate buffer, pH 8.0, 7 M guanidium-hydrochloride, 5 mM imidazole, 20 mM thioglycerole. Insoluble material is pelleted by centrifugation and the supernatant is applied to Ni-nitrilotriacetic acid (Ni-NTA) metal-affinity chromatography: The column is washed with several bed volumes of lysis buffer followed by washes with a) 100 mM sodium-phosphate buffer, pH 8.0, 10 mM Tris-HCl, pH 8.0, 8 M urea, 20 mM thioglycerole; b) 100 mM sodium-phosphate buffer, pH 8.0, 0.5% sodium-dodecylsulfate (SDS), 20 mM thioglycerole; and c) 100 mM sodium-phosphate buffer, pH 8.0, 0.1% SDS, 20 mM thioglycerole. Finally, bound antigen is eluted using 100 mM sodium-phosphate buffer, pH 5.0, 0.1% SDS, 20 mM thioglycerole, under acid conditions, and stored in the same buffer at 4° C.

Generation of Polyclonal Antibodies:

a) Immunization

For immunization, a fresh emulsion of the protein solution (100 µg/ml protein ARMET) and complete Freund's adjuvant at the ratio of 1:1 is prepared. Each rabbit is immunized with 1 ml of the emulsion at days 1, 7, 14 and 30, 60 and 90. Blood is drawn and resulting anti-ARMET serum used for further experiments as described in examples 3 and 4.

b) Purification of IgG (immunoglobulin G) from Rabbit Serum by Sequential Precipitation with Caprylic Acid and Ammonium Sulfate One volume of rabbit serum is diluted with 4 volumes of acetate buffer (60 mM, pH 4.0). The pH is adjusted to 4.5 with 2 M Tris-base. Caprylic acid (25 µl/ml of diluted sample) is added drop-wise under vigorous stirring. After 30 min the sample is centrifuged (13 000×g, 30 min, 4° C.), the pellet discarded and the supernatant collected. The pH of the supernatant is adjusted to 7.5 by the addition of 2 M Tris-base and filtered (0.2 µm).

The immunoglobulin in the supernatant is precipitated under vigorous stirring by the drop-wise addition of a 4 M ammonium sulfate solution to a final concentration of 2 M. The precipitated immunoglobulins are collected by centrifugation (8000×g, 15 min, 4° C.).

The supernatant is discarded. The pellet is dissolved in 10 mM NaH₂PO₄/NaOH, pH 7.5, 30 mM NaCl and exhaustively dialyzed. The dialysate is centrifuged (13 000×g, 15 min, 4° C.) and filtered (0.2 µm).

Biotinylation of Polyclonal Rabbit IgG:

Polyclonal rabbit IgG is brought to 10 mg/ml in 10 mM NaH₂PO₄/NaOH, pH 7.5, 30 mM NaCl. Per ml IgG solution 50 µl Biotin-N-hydroxysuccinimide (3.6 mg/ml in DMSO) are added. After 30 min at room temperature, the sample is chromatographed on Superdex 200 (10 mM NaH$_2$PO$_4$/NaOH, pH 7.5, 30 mM NaCl). The fraction containing biotinylated IgG are collected. Monoclonal antibodies have been biotinylated according to the same procedure.

Digoxygenylation of Polyclonal Rabbit IgG:

Polyclonal rabbit IgG is brought to 10 mg/ml in 10 mM NaH$_2$PO$_4$/NaOH, 30 mM NaCl, pH 7.5. Per ml IgG solution 50 µl digoxigenin-3-O-methylcarbonyl-ε-aminocaproic acid-N-hydroxysuccinimide ester (Roche Diagnostics, Mannheim, Germany, Cat. No. 1 333 054) (3.8 mg/ml in DMSO) are added. After 30 min at room temperature, the sample is chromatographed on SUPERDEX 200 (10 mM NaH$_2$PO$_4$/NaOH, pH 7.5, 30 mM NaCl). The fractions containing digoxigenylated IgG are collected. Monoclonal antibodies have been labeled with digoxigenin according to the same procedure.

Example 3

ELISA for the Measurement of ARMET in Human Serum and Plasma Samples or Other Body Fluids For detection of ARMET in human serum or plasma, a sandwich ELISA is developed. For capture and detection of the antigen, aliquots of the anti-ARMET polyclonal antibody (see Example 2) are conjugated with biotin and digoxygenin, respectively.

Streptavidin-coated 96-well microtiter plates are incubated with 100 µl biotinylated anti-ARMET polyclonal antibody for 60 min at 10 µg/ml in 10 mM phosphate, pH 7.4, 1% BSA, 0.9% NaCl and 0.1% TWEEN 20. After incubation, plates are washed three times with 0.9% NaCl, 0.1% TWEEN 20. Wells are then incubated for 2 h with either a serial dilution of the recombinant protein (see Example 2) as standard antigen or with diluted plasma samples from patients. After binding of ARMET, plates are washed three times with 0.9% NaCl, 0.1% TWEEN 20. For specific detection of bound ARMET, wells are incubated with 100 µl of digoxygenylated anti-ARMET polyclonal antibody for 60 min at 10 µg/ml in 10 mM phosphate, pH 7.4, 1% BSA, 0.9% NaCl and 0.1% TWEEN 20. Thereafter, plates are washed three times to remove unbound antibody. In a next step, wells are incubated with 20 mU/ml anti-digoxigenin-POD conjugates (Roche Diagnostics GmbH, Mannheim, Germany, Catalog No. 1633716) for 60 min in 10 mM phosphate, pH 7.4, 1% BSA, 0.9% NaCl and 0.1% TWEEN 20. Plates are subsequently washed three times with the same buffer. For detection of antigen-antibody complexes, wells are incubated with 100 µl ABTS solution (Roche Diagnostics GmbH, Mannheim, Germany, Catalog No. 11685767) and OD is measured after 30-60 min at 405 nm with an ELISA reader.

Example 4

ARMET as a Serum Marker for Lung Cancer

Samples derived from 366 well-characterized lung cancer patients (148 adeno-CA, 87 squamous cell CA, 44 small cell CA, 87 other CA of the lung) with the UICC classification given in Table 3 are used

TABLE 3

| Study population | |
|---|---|
| Stage according to UICC | Number of samples |
| UICC I/II | 167 |
| UICC III | 112 |
| UICC IV | 58 |
| unstaged | 29 |
| obviously healthy blood donors | 50 |

The level of ARMET in the LC samples of Table 3 is evaluated in comparison to 50 control samples obtained from obviously healthy individuals (=control cohort), with an AUC of 0.86 (FIG. 2).

Example 5

ARMET as a Serum Marker for Colorectal Cancer (CRC)

Samples derived from 50 well-characterized colorectal cancer patients with the UICC classification given in Table 3 are used

TABLE 4

| Study population | |
|---|---|
| Stage according to UICC | Number of samples |
| UICC I/II | 26 |
| UICC III | 17 |
| UICC IV | 6 |
| unstaged | 1 |
| obviously healthy blood donors | 50 |

The level of ARMET in the CRC samples of Table 4 is evaluated in comparison to 50 control samples obtained from obviously healthy individuals (=control cohort), resulting in an AUC of 0.75 (FIG. 3)

Example 6

ARMET as a Serum Marker for Breast Cancer (BC)

Samples derived from 49 well-characterized breast cancer patients with the UICC classification given in Table 3 are used

TABLE 5

| Study population | |
|---|---|
| Stage according to UICC | Number of samples |
| UICC I/II | 26 |
| UICC III | 11 |
| UICC IV | 13 |
| obviously healthy blood donors | 50 |

The level of ARMET in the BC samples of Table 5 is evaluated in comparison to 50 control samples obtained from obviously healthy individuals (=control cohort), resulting in an AUC of 0.86 (FIG. 4).

Example 7

ARMET as a Serum Marker for Ovarian Cancer (OC)

Samples derived from 43 well-characterized ovarian cancer (OC) patients with the UICC classification given in Table 3 are used

TABLE 6

| Study population | |
|---|---|
| Stage according to UICC | Number of samples |
| UICC I/II | 12 |
| UICC III | 21 |
| UICC IV | 10 |
| obviously healthy blood donors | 50 |

The level of ARMET in the OC samples of Table 6 is evaluated in comparison to 50 control samples obtained from obviously healthy individuals (=control cohort), resulting in an AUC of 0.91 (FIG. 5)

Example 8

Western Blotting for the Detection of ARMET in Human Lung Cancer (LC) Tissue using Polyclonal Antibody as Generated in Example 2

Figure 1:
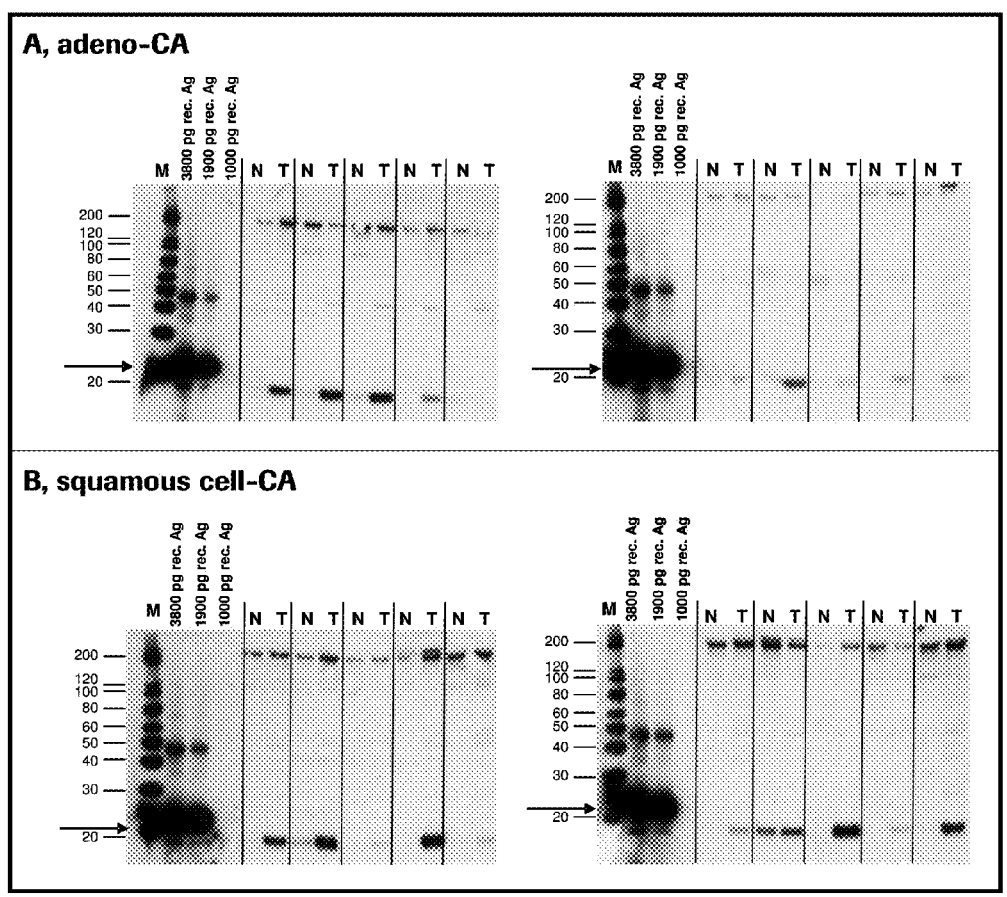
FIG. 1 shows Western Blot analyses of lung cancer tissue lysates. 15 μg total protein of 10 adeno CA (panel A) and 10 squamous cell CA tissue lysates (panel B) and matched control tissue lysates were analyzed as described in Example 5. M=molecular weight marker; T=tumor tissue lysate; N=matched control tissue lysate; rec Ag=recombinantly produced ARMET; arrows indicate the position of ARMET.

Tissue lysates from tumor samples and healthy control samples are prepared as described in Example 1, "Tissue preparation".
SDS-PAGE and Western-Blotting are carried out using reagents and equipment of Invitrogen, Karlsruhe, Germany. For each tissue sample tested, 15 µg of tissue lysate are diluted in reducing NuPAGE (Invitrogen) SDS sample buffer and heated for 10 min at 95° C. Samples are run on 4-12% NuPAGE gels (Tris-Glycine) in the MES running buffer system. The gel-separated protein mixture is blotted onto nitrocellulose membranes using the Invitrogen XCell II Blot Module (Invitrogen) and the NuPAGE transfer buffer system. The membranes are washed 3 times in PBS/0.05% TWEEN-20 and blocked with Roti-Block blocking buffer (A151.1; Carl Roth GmbH, Karlsruhe, Germany) for 2 h. The primary antibody, polyclonal rabbit anti-ARMET serum (generation described in Example 2), is diluted 1:10,000 in Roti-Block blocking buffer and incubated with the membrane for 1 h. The membranes are washed 6 times in PBS/0.05% TWEEN-20. The specifically bound primary rabbit antibody is labeled with an POD-conjugated polyclonal sheep anti-rabbit IgG antibody, diluted to 10 mU/ml in 0.5× Roti-Block blocking buffer. After incubation for 1 h, the membranes are washed 6 times in PBS/0.05% TWEEN-20. For detection of the bound POD-conjugated anti-rabbit antibody, the membrane is incubated with the Lumi-Light$^{PLUS}$ Western Blotting Substrate (Order-No. 2015196, Roche Diagnostics GmbH, Mannheim, Germany) and exposed to an autoradiographic film.
Signal intensity for ARMET is increased in 18 out of 20 tumor tissue lysates as obtained from 20 different LC patients (FIG. 1). Thus, the increased abundance of ARMET in tumor tissue as detected by MALDI in example 1 is clearly confirmed by Western Blotting analyses.

Example 9

ARMET in Epithelial Lining Fluid (ELF)—Bronchoscopic Microsampling

Bronchoscopic microsampling (BMS) offers the possibility to collect epithelial lining fluid (ELF) near small pulmonary nodules in a largely non-invasive manner. Subsequently, it is possible to measure concentrations of tumor markers in ELF in order to identify a malignant nodule.
The BMS probe (Olympus Medical Systems Corp. Tokyo, Japan, Cat.-No.: BC-402C) is inserted into the lungs through the bronchoscope and consists of an outer polyethylene sheath and an inner cotton probe attached to a stainless steel guide. The inner probe is advanced to the proximity of the nodule and BMS is performed for a few seconds. Afterwards, the inner probe is withdrawn into the outer sheath and both devices are withdrawn simultaneously. The cotton tip is cut off and directly frozen at −80° C. For the determination, ELF is eluted from the cotton tip and can be analyzed subsequently. The concentration of ARMET is determined in ELF with the ELISA as described in Example 2.

Example 10

Immunostaining of ARMET with Pab K4344

Paraffin-embedded tissues were obtained from Roche tumor bank (MML, Pharma Research Penzberg). Tissues were cut into 2 µm serial sections, deparaffinized in xylene (3×5 min) and rehydrated through a series of graded ethanol followed by two washing steps with deionized water and PBS (1×2 min). Antigen retrieval was performed with Retrivit pH 4.0 (Biogenex) for 20 min at 97° C.-100° C. Slides were let cool down for 20 min and rinsed with PBS (2×1 min). Endogenous peroxidase activity was blocked by incubation in 3% H2O2 in PBS for 5 min, the slides were then rinsed twice with PBS followed by TBS+TWEEN 20 (LabVision 1666789) once for 3 min. Blocking of immunoglobulin unspecific binding was performed with horse serum 1% in PBS (Horse—Blocking Serum, Vectastain ABC kit, Elite Universal, Vector PK6200) for 20 min at room temperature. Endogenous biotin was blocked with Biotin Blocking System (Dako X0590) following the manufactory's instruction. For ARMET specific staining sections were incubated with the polyclonal antibody K4344 diluted at 3 µg/ml in Antiboby-Diluent (Dako S2022) overnight at 4° C. Slides were washed with TBS+TWEEN 20 (LabVision 1666789) (3×2 min) and then incubated with the biotinylated secondary antibody (1 drop in 5 ml of PBS+1% horse serum) (Vectastain ABC kit, Elite Universal, Vector PK6200) for 30 min at room temperature. After washing with TBS+TWEEN 20 (3×2 min) sections were incubated with ABC reagent (1 drop Reagent A plus 1 drop Reagent B in 5 ml PBS) for 30 min at room temperature. Slides were washed with TBS+TWEEN 20 (2×2 min) and finally reacted with diaminobenzidine chromogen solution (DAB plus, LabVision TA-125-HDX) for 10 min., after rinsing with distilled water they were counterstained with hematoxylin and mounted.
Rabbit IgG fraction (Dako X0903) was used as negative control.

TABLE 7

| ARMET expression in tumor | | | | |
|---|---|---|---|---|
| | | ARMET expression | | |
| Tumor | No. of cases tested | Positive | Weak | Negative |
| Lung | 29 | 24 | 1 | 4 |
| Colon | 20 | 17 | 2 | 1 |
| Breast | 16 | 14 | 1 | 1 |
| Head and neck | 20 | 18 | 1 | 1 |
| Melanoma | 12 | 11 | 0 | 1 |
| Pancreas | 8 | 8 | 0 | 0 |
| Kidney | 7 | 7 | 0 | 0 |
| Ovary | 11 | 11 | 0 | 0 |
| Prostate | 11 | 11 | 0 | 0 |

What is claimed is:

1. A method for assessing lung cancer in vitro in a patient, the method comprising:
   contacting, in vitro, a portion of a lung tissue sample obtained from the patient with an antibody having specific binding affinity for arginine-rich, mutated in early stage tumors (ARMET) protein and/or fragments thereof, thereby forming a complex of the antibody and ARMET protein and/or fragment thereof, the antibody having a detectable label;
   quantifying a signal from the detectable label of the antibody comprising the complex formed in said step of contacting, the signal being proportional to an ARMET concentration in the sample, whereby ARMET concentration in the sample is calculated;
   comparing the ARMET concentration in the sample to a control concentration; and
   diagnosing lung cancer in the patient if the ARMET concentration in the sample is greater than the control concentration.

2. The method of claim 1 further comprising the steps of:
   contacting, in vitro, a portion of the sample obtained from the patient with an antibody having specific binding affinity for an additional marker of cancer, thereby forming a complex of the antibody having specific binding affinity for the additional marker and the additional marker of cancer, the antibody having specific binding affinity for the additional marker having a detectable label;
   quantifying a signal resultant from the detectable label of the antibody having specific binding affinity for the additional marker comprising the complex formed in said step of contacting, the signal being proportional to the additional marker of cancer concentration in the sample; and
   comparing the additional marker of cancer concentration in the sample to a control concentration for the additional marker of cancer, wherein said step of diagnosing further comprises diagnosing lung cancer in the patient if both ARMET concentration in the sample is greater than the control concentration and the additional marker of cancer concentration is greater than the control concentration for the additional marker of cancer.

3. The method according to claim 2, wherein the additional marker is selected from the group consisting of soluble 30 kDa fragment of cytokeratin 19 (Cyfra 21-1), carcinoembryogenic antigen (CEA), carbohydrate antigen 19-9 (CA 19-9), squamous cell carcinoma antigen (SCC), carbohydrate antigen 125 (CA 125), neuron-specific enolase (NSE), pro-gastrin-releasing peptide (proGRP), prostate specific antigen (PSA), and nicotinamide N-methyltransferase (NNMT).

4. A method of managing treatment of a patient suspected of having lung cancer, the method comprising:
   contacting, in vitro, a portion of a lung tissue sample obtained from the patient prior to treatment with an antibody having specific binding affinity for arginine-rich, mutated in early stage tumors (ARMET) protein and/or fragments thereof, thereby forming a complex of the antibody and ARMET protein and/or fragment thereof, the antibody having a detectable label;
   quantifying a signal from the detectable label of the antibody comprising the complex formed in said step of contacting, the signal being proportional to ARMET concentration in the sample obtained prior to treatment, whereby ARMET concentration in the sample is calculated;
   comparing the ARMET concentration in the sample to a control concentration; and
   treating the patient for lung cancer if the ARMET concentration in the sample is greater than the control concentration.

5. The method according to claim 4, wherein treatment comprises surgical resection, chemotherapy, or both.

6. The method of claim 4 further comprising the steps of:
   contacting, in vitro, a portion of the sample obtained from the patient prior to treatment with an antibody having specific binding affinity for an additional marker of cancer, thereby forming a complex of the antibody having specific binding affinity for the additional marker and the additional marker of cancer, the antibody having specific binding affinity for the additional marker having a detectable label;
   quantifying a signal from the detectable label of the antibody having specific binding affinity for the additional marker comprising the complex formed in said step of contacting, the signal being proportional to the additional marker of cancer concentration in the sample obtained prior to treatment; and
   comparing the additional marker of cancer concentration in the sample to a control concentration for the additional marker of cancer, wherein said step of treating the patient further comprises treating the patient for lung cancer if both ARMET concentration in the sample is greater than the control concentration and the additional marker of cancer concentration is greater than the additional control concentration.

7. The method of claim 4 further comprising the steps of:
   contacting, in vitro, a portion of a sample obtained from the patient following said step of treating, with the antibody, whereby the complex forms;
   quantifying a signal from the detectable label of the antibody comprising the complex formed in said step of contacting, the signal being proportional to ARMET concentration in the sample obtained following said step of treating, whereby ARMET concentration in the sample obtained following said step of treating is calculated; and
   identifying the patient as successfully treated by said step of treating if the ARMET concentration in the sample obtained following treatment is less than the ARMET concentration in the sample obtained prior to treatment.

8. The method of claim 7 further comprising the step of discontinuing treatment of the patient if the ARMET concentration in the sample obtained following treatment is less than the ARMET concentration in the sample obtained prior to treatment.

9. The method according to claim 8, wherein the additional marker of cancer is selected from the group consisting of soluble 30 kDa fragment of cytokeratin 19 (Cyfra 21-1), carcinoembryogenic antigen (CEA), carbohydrate antigen 19-9 (CA 19-9), squamous cell carcinoma antigen (SCC), carbohydrate antigen 125 (CA 125), neuron-specific enolase (NSE), pro-gastrin-releasing peptide (proGRP), prostate specific antigen (PSA), and nicotinamide N-methyltransferase (NNMT).

* * * * *

SEQUENCE LISTING

<160> NUMBER OF SEQ ID NOS: 4

<210> SEQ ID NO 1
<211> LENGTH: 179
<212> TYPE: PRT
<213> ORGANISM: Homo sapiens

<400> SEQUENCE: 1

| Met | Trp | Ala | Thr | Gln | Gly | Leu | Ala | Val | Ala | Leu | Ala | Leu | Ser | Val | Leu |
|---|---|---|---|---|---|---|---|---|---|---|---|---|---|---|---|
| 1 | | | | 5 | | | | | 10 | | | | | 15 | |

| Pro | Gly | Ser | Arg | Ala | Leu | Arg | Pro | Gly | Asp | Cys | Glu | Val | Cys | Ile | Ser |
|---|---|---|---|---|---|---|---|---|---|---|---|---|---|---|---|
| | | | 20 | | | | | 25 | | | | | 30 | | |

| Tyr | Leu | Gly | Arg | Phe | Tyr | Gln | Asp | Leu | Lys | Asp | Arg | Asp | Val | Thr | Phe |
|---|---|---|---|---|---|---|---|---|---|---|---|---|---|---|---|
| | | | 35 | | | | | 40 | | | | 45 | | | |

| Ser | Pro | Ala | Thr | Ile | Glu | Asn | Glu | Leu | Ile | Lys | Phe | Cys | Arg | Glu | Ala |
|---|---|---|---|---|---|---|---|---|---|---|---|---|---|---|---|
| | 50 | | | | | 55 | | | | | 60 | | | | |

| Arg | Gly | Lys | Glu | Asn | Arg | Leu | Cys | Tyr | Tyr | Ile | Gly | Ala | Thr | Asp | Asp |
|---|---|---|---|---|---|---|---|---|---|---|---|---|---|---|---|
| 65 | | | | | 70 | | | | | 75 | | | | | 80 |

| Ala | Ala | Thr | Lys | Ile | Ile | Asn | Glu | Val | Ser | Lys | Pro | Leu | Ala | His | His |
|---|---|---|---|---|---|---|---|---|---|---|---|---|---|---|---|
| | | | | 85 | | | | | 90 | | | | | 95 | |

| Ile | Pro | Val | Glu | Lys | Ile | Cys | Glu | Lys | Leu | Lys | Lys | Lys | Asp | Ser | Gln |
|---|---|---|---|---|---|---|---|---|---|---|---|---|---|---|---|
| | | | | 100 | | | | | 105 | | | | | 110 | |

| Ile | Cys | Glu | Leu | Lys | Tyr | Asp | Lys | Gln | Ile | Asp | Leu | Ser | Thr | Val | Asp |
|---|---|---|---|---|---|---|---|---|---|---|---|---|---|---|---|
| | | | 115 | | | | | 120 | | | | | 125 | | |

| Leu | Lys | Lys | Leu | Arg | Val | Lys | Glu | Leu | Lys | Lys | Ile | Leu | Asp | Asp | Trp |
|---|---|---|---|---|---|---|---|---|---|---|---|---|---|---|---|
| | 130 | | | | | 135 | | | | | 140 | | | | |

| Gly | Glu | Thr | Cys | Lys | Gly | Cys | Ala | Glu | Lys | Ser | Asp | Tyr | Ile | Arg | Lys |
|---|---|---|---|---|---|---|---|---|---|---|---|---|---|---|---|
| 145 | | | | | 150 | | | | | 155 | | | | | 160 |

| Ile | Asn | Glu | Leu | Met | Pro | Lys | Tyr | Ala | Pro | Lys | Ala | Ala | Ser | Ala | Arg |
|---|---|---|---|---|---|---|---|---|---|---|---|---|---|---|---|
| | | | | 165 | | | | | 170 | | | | | 175 | |

Thr Asp Leu

<210> SEQ ID NO 2
<211> LENGTH: 100
<212> TYPE: DNA
<213> ORGANISM: Artificial Sequence
<220> FEATURE:
<223> OTHER INFORMATION: Description of Artificial Sequence: Synthetic
      forward primer LC56for-EcoRI

<400> SEQUENCE: 2
acgtacgtga attcattaaa gaggagaaat taactatatg agaggatcgc atcaccatca      60
ccatcacatt gaaggccgta ggaggatgtg ggccacgcag                           100

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      reverse primer LC56rev-BamHI

<400> SEQUENCE: 3
acgtacgtgg atcctcatta caaatcggtc cgtgcactgg                            40

<210> SEQ ID NO 4
<211> LENGTH: 14
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 4

Met Arg Gly Ser His His His His His His Ile Glu Gly Arg
1               5                   10
```